(12) United States Patent
Lahm et al.

(10) Patent No.: US 9,023,850 B2
(45) Date of Patent: May 5, 2015

(54) NEMATOCIDAL SULFONAMIDES

(75) Inventors: George Philip Lahm, Wilmington, DE (US); Thomas Francis Pahutski, Jr., Elkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/878,261

(22) PCT Filed: Oct. 5, 2011

(86) PCT No.: PCT/US2011/054868
§ 371 (c)(1),
(2), (4) Date: Apr. 8, 2013

(87) PCT Pub. No.: WO2012/054233
PCT Pub. Date: Apr. 26, 2012

(65) Prior Publication Data
US 2013/0190172 A1    Jul. 25, 2013

Related U.S. Application Data

(60) Provisional application No. 61/394,080, filed on Oct. 18, 2010.

(51) Int. Cl.
*C07D 487/04* (2006.01)
*A01N 43/90* (2006.01)

(52) U.S. Cl.
CPC .............. *A01N 43/90* (2013.01); *C07D 487/04* (2013.01)

(58) Field of Classification Search
CPC ............................... A01N 43/90; C07D 487/04
USPC ......... 504/100, 136, 137, 139, 235, 246, 252,
504/253, 276; 514/247, 248, 252.05, 256,
514/259.1, 259.3, 265.1, 300, 303, 359,
514/397, 601, 603; 546/113, 121;
548/302.7, 335.1; 564/80, 81, 84, 85,
564/86, 89; 424/405
See application file for complete search history.

(56) References Cited

U.S. PATENT DOCUMENTS

| | | | |
|---|---|---|---|
| 8,623,890 B2 * | 1/2014 | Lahm et al. | 514/300 |
| 2014/0221203 A1 * | 8/2014 | Lahm et al. | 504/100 |
| 2014/0243201 A1 * | 8/2014 | Klingelhoefer et al. | 504/206 |

FOREIGN PATENT DOCUMENTS

| | | | | |
|---|---|---|---|---|
| EP | 0244166 A3 * | 4/1987 | | C07D 487/04 |
| WO | WO2010/087294 A1 * | 8/2010 | | C07D 487/04 |

* cited by examiner

*Primary Examiner* — Jane C Oswecki
(74) *Attorney, Agent, or Firm* — Roman Kucharczyk

(57) ABSTRACT

Disclosed are compounds of Formula 1, N-oxides, and salts thereof,

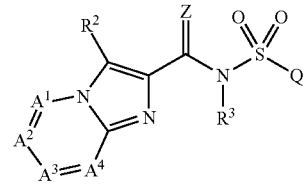

wherein
Z is O or S;
$A^1$, $A^2$, $A^3$ and $A^4$ are independently N or $CR^1$, provided that only one of $A^1$, $A^2$, $A^3$ and $A^4$ is N; and
$R^1$, $R^2$, $R^3$ and Q are as defined in the disclosure.

Also disclosed are compositions containing the compounds of Formula 1 and methods for controlling a parasitic nematode comprising contacting the parasitic nematode or its environment with a biologically effective amount of a compound or a composition of the invention.

14 Claims, No Drawings

NEMATOCIDAL SULFONAMIDES

FIELD OF THE INVENTION

This invention relates to certain sulfonamides, their N-oxides, salts and compositions suitable for agronomic and nonagronomic uses, and methods of their use for controlling parasitic nematodes in both agronomic and nonagronomic environments.

BACKGROUND OF THE INVENTION

The control of plant-parasitic nematodes is extremely important in achieving high crop efficiency. Nematode-induced root damage can cause significant reduction in crop yields and quality and thereby result in increased costs to the consumer. Due to widespread development of resistance to anthelmintic agents in nematode parasites, nematodes continue to cause problems in livestock despite the available chemical therapeutic agents. The need continues for new compounds which are more effective, less costly, less toxic, environmentally safer or have different modes of action.

European Patent Application Publication No. 0 244 166 A2 discloses compounds of Formula i as herbicides

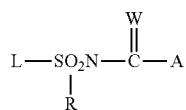

wherein, inter alia, R is H or an organic substituent, W is O or S, L is an aryl or heteroaryl moiety, and A is selected from a list of bi-, tri- and quadricyclic heterocyclic groups.

The compounds of the present invention are not disclosed in this publication.

SUMMARY OF THE INVENTION

This invention is directed to compounds of Formula 1 (including all stereoisomers), N-oxides, and salts thereof, and compositions containing them and their use for controlling a parasitic nematode:

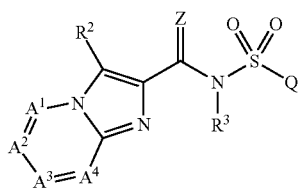

wherein
Z is O or S;
$A^1$, $A^2$, $A^3$ and $A^4$ are independently N or $CR^1$, provided that only one of $A^1$, $A^2$, $A^3$ and $A^4$ is N;
each $R^1$ is independently H, halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C(X)R^7$, $C(O)OR^8$, $C(O)NR^{11}R^{12}$, $S(O)_mR^9$ or $S(O)_2NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^7$, $C(O)OR^8$, $C(O)NR^{11}R^{12}$, $S(O)_mR^9$ and $S(O)_2NR^{11}R^{12}$;
$R^2$ is H, halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C(X)R^7$, $C(O)OR^8$, $C(O)NR^{11}R^{12}$, $S(O)_mR^9$ or $S(O)NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^7$, $C(O)OR^8$, $C(O)NR^{11}R^{12}$, $S(O)_mR^9$ and $S(O)_2NR^{11}R^{12}$;
$R^3$ is H, $C(X)R^7$, $C(O)OR^8$, $C(O)NR^{11}R^{12}$, $S(O)_mR^9$ or $S(O)_2NR^{11}R^{12}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with 1 to 4 substituents independently selected from the group consisting of halogen, cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$; or $C_1$-$C_6$ alkyl substituted with 1 or 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$ and $S(O)_2NR^{11}R^{12}$;
Q is phenyl, naphthalenyl, a 5- or 6-membered heteroaromatic ring or an 8- to 10-membered aromatic bicyclic ring system, each optionally substituted with 1 to 5 substituents independently selected from the group consisting of halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_1$-$C_6$ haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^8$, $N(R^{10})C(O)NR^{11}R^{12}$, $N(R^{10})S(O)_2R^9$, $N(R^{10})S(O)_2NR^{11}R^{12}$ and $R^{14}$;
each X is independently O or S;
each $R^4$ is independently H, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(O)NR^{11}R^{12}$ or $S(O)_mR^9$; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;
each $R^{4a}$ is independently H, $NR^{5a}R^{6a}$, $C_1$-$C_6$ alkyl or $C_1$-$C_6$ haloalkyl;
each $R^5$ is independently H, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(O)NR^{11}R^{12}$, $S(O)_mR^9$ or $S(O)_2NR^{11}R^{12}$; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1$-$C_6$ alkyl;

each $R^6$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C(X)R^{7a}$, $C(O)OR^{8a}$, $C(O)NR^{11}R^{12}$, $S(O)_mR^{9a}$ or $S(O)NR^{11}R^{12}$;

each $R^{6a}$ is independently H, $C_1$-$C_6$ alkyl, $C(O)R^{13}$ or $C(O)OR^{13}$;

each $R^7$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{7a}$ is independently $C_1$-$C_6$ alkyl or $C_1$-$C_6$ haloalkyl;

each $R^8$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_{14}R^{9a}$, $S(O)_2NR^{11}R^{12}$, $NR^{5a}R^{6a}$, $OC(O)R^{7a}$ and $N(R^{10})C(O)R^{7a}$;

each $R^{8a}$ is independently $C_1$-$C_6$ alkyl or $C_1$-$C_6$ haloalkyl;

each $R^9$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{9a}$ is independently $C_1$-$C_6$ alkyl or $C_1$-$C_6$ haloalkyl;

each $R^{10}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{11}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11a}R^{12}$, $OR^{4a}$, $C_2$-$C_6$ alkoxyalkyl, $S(O)_mR^{9a}$, $S(O)_2NR^{11a}R^{12}$, $NR^{5a}R^{6a}$, $OC(O)R^{7a}$ and $N(R^{10})C(O)R^{7a}$;

each $R^{11a}$ is independently $C_1$-$C_6$ alkyl, $C_2$-$C_6$ alkenyl or $C_2$-$C_6$ alkynyl;

each $R^{12}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C_3$-$C_7$ cycloalkyl;

each $R^{13}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$;

each $R^{14}$ is independently $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or $C_1$-$C_6$ alkyl, $C_2$-$C_6$ alkenyl or $C_2$-$C_6$ alkynyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$; and each m is independently 0, 1 or 2.

This invention also provides a composition comprising a compound of Formula 1, an NV-oxide, or a salt thereof and at least one additional component selected from the group consisting of surfactants, solid diluents and liquid diluents. In one embodiment, this invention also provides a composition for controlling a parasitic nematode comprising a compound of Formula 1, an N-oxide, or a salt thereof, and at least one additional component selected from the group consisting of surfactants, solid diluents and liquid diluents, said composition optionally further comprising at least one additional biologically active compound or agent.

This invention provides a method for controlling a parasitic nematode comprising contacting the parasitic nematode or its environment with a biologically effective amount of a compound of Formula 1, an N-oxide, or a salt thereof, (e.g., as a composition described herein). This invention also relates to such method wherein the parasitic nematode or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent.

This invention also provides a method for protecting a seed from a parasitic nematode comprising contacting the seed with a biologically effective amount of a compound of Formula 1, an N-oxide, or a salt thereof, (e.g., as a composition described herein). This invention also relates to the treated seed.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used to in the present disclosure and claims, the term "nematode" refers to a living organism of the Phylum Nematoda. As generally defined, a "parasite" lives or grows inside or feeds on another living organism (such as a plant, animal or human) described as the "host". As referred to in the present disclosure and claims a "parasitic nematode" is particularly a nematode that injures or damages tissue or causes other forms of disease in plants, animals (particularly vertebrates) or humans.

A parasite "infestation" refers to the presence of parasites in numbers that pose a risk to plants, humans or animals. The presence can be in the environment, e.g., in a human or animal house, or surrounding property or structures, on an agricultural crop or other type of plant, in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

As referred to in the present disclosure and claims, the terms "parasiticidal" and "parasiticidally" refers to observable effects on a parasitic nematode to provide protection of a plant, animal or human from the nematode. Parasiticidal effects typically relate to diminishing the occurrence or activity of the target parasitic nematode. Such effects on the nematode include necrosis, death, retarded growth, diminished mobility or lessened ability to remain on or in the host plant, animal or human, reduced feeding and inhibition of reproduction. These effects on parasitic nematodes provide control (including prevention, reduction or elimination) of parasitic infestation or infection of the plant, animal or human. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from a parasitic nematode by administering a parasiticidally effective (i.e. biologically effective) amount of a compound of the invention, typically in the form of a composition formulated for veterinary use, to the animal to be protected.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than one double bond such as 1,3- and 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $Cl_2CH_2$, $CF_3CH_2$ and $CF_3CCl_2$. The terms "haloalkoxy", "haloalkenyl", "haloalkynyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$.

The chemical abbreviation C(O) as used herein represents a carbonyl moiety. For example, $C(O)CH_3$ represents an acetyl group. The chemical abbreviations $CO_2$ and C(O)O as used herein represent an ester moiety. For example, $CO_2Me$ and C(O)OMe represent a methyl ester.

"OCN" means —O—C≡N, and "SCN" means —S—C≡N.

The definition "$A^1$, $A^2$, $A^3$ and $A^4$ are independently N or $CR^1$, provided that only one of $A^1$, $A^2$, $A^3$ and $A^4$ is N" means that the variables $A^1$, $A^2$, $A^3$ and $A^4$ can exist in four possible combinations, i.e. $A^1$ is N and $A^2$, $A^3$ and $A^4$ are independently $CR^1$, or $A^2$ is N and $A^1$, $A^3$ and $A^4$ are independently $CR^1$, or $A^3$ is N and $A^1$, $A^2$ and $A^4$ are independently $CR^1$, or $A^4$ is N and $A^1$, $A^2$ and $A^3$ are independently $CR^1$.

The total number of carbon atoms in a substituent group is indicated by the "$C_i$-$C_j$" prefix where i and j are numbers from 1 to 14. $C_2$ alkoxyalkyl designates $CH_3OCH$; $C_3$ alkoxyalkyl designates, for example, $C_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g., $R^1$, n is 0, 1, 2, 3 or 4. When a group contains a substituent which can be hydrogen, for example $R^2$ or $R^3$, then when this substituent is taken as hydrogen, it is recognized that this is equivalent to said group being unsubstituted. When a variable group is shown to be optionally attached to a position, for example $(R^v)_r$ in U-29 of Exhibit 1 wherein r may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent Q) is carbocyclic or heterocyclic. The term "ring system" denotes two or more fused rings. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "heterocyclic ring system" denotes a ring system in which at least one ring of the ring system is a heterocyclic ring. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which (4n+2) π electrons, where n is a positive integer, are associated with the ring to comply with Hückel's rule. When a fully unsaturated heterocyclic ring satisfies Hückel's rule, then said ring is also called a "heteroaromatic ring". The term "heteroaromatic ring system" denotes a heterocyclic ring system in which at least one ring of the ring system is aromatic.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

When a substituent is a 5- or 6-membered nitrogen-containing heteroaromatic ring, it may be attached to the remainder of Formula 1 though any available carbon or nitrogen ring atom, unless otherwise described.

An example of phenyl optionally substituted with one to five substituents is the ring illustrated as U-1 in Exhibit 1, wherein $R^v$ is as defined in the Summary of the Invention for $R^1$, $R^2$, $R^3$ or Q and r is an integer from 0 to 5.

Examples of an optionally substituted 5- or 6-membered heteroaromatic ring include the rings U-2 through U-61 illustrated in Exhibit 1 wherein $R^v$ is any substituent as defined in the Summary of the invention for $R^1$, $R^2$, $R^3$ or Q and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1
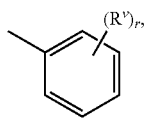 U-1
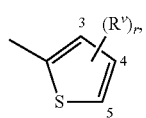 U-2
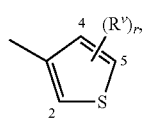 U-3
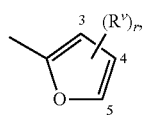 U-4
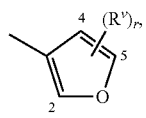 U-5
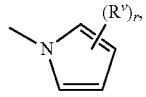 U-6
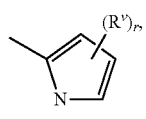 U-7
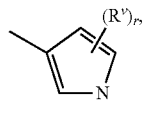 U-8
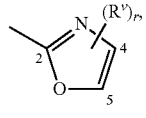 U-9
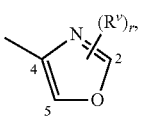 U-10
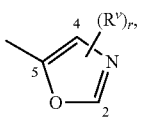 U-11
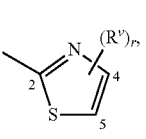 U-12
-continued
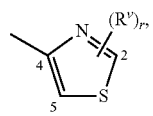 U-13
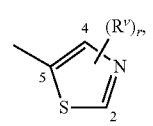 U-14
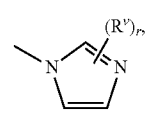 U-15
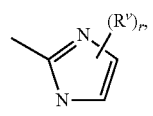 U-16
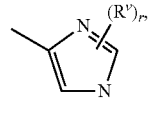 U-17
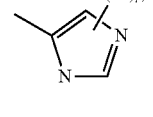 U-18
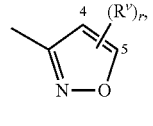 U-19
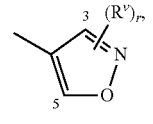 U-20
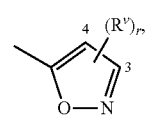 U-21
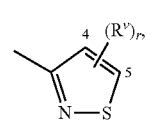 U-22
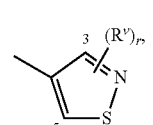 U-23
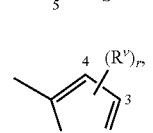 U-24
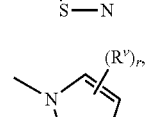 U-25
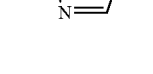

| | | |
|---|---|---|
| 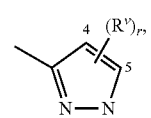 | U-26 | 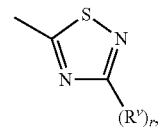 U-38 |
| 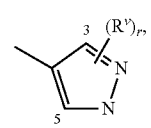 | U-27 | 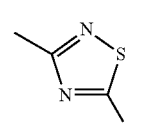 U-39 |
| 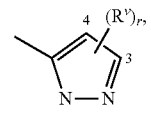 | U-28 | 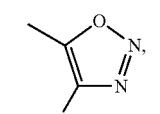 U-40 |
| 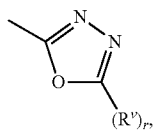 | U-29 | 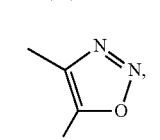 U-41 |
| 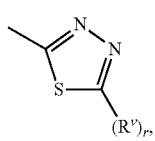 | U-30 | 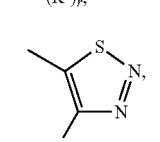 U-42 |
| 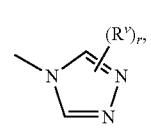 | U-31 | 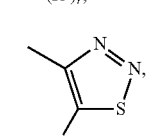 U-43 |
| 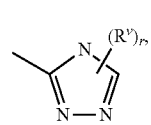 | U-32 | 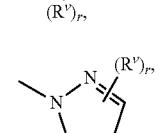 U-44 |
| 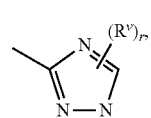 | U-33 | 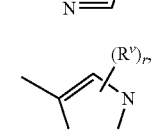 U-45 |
| 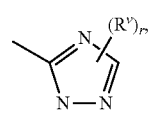 | U-34 | 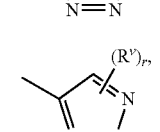 U-46 |
| 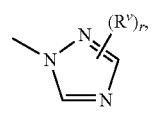 | U-35 | 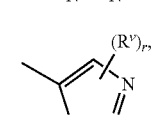 U-47 |
| 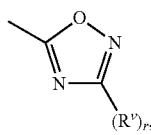 | U-36 | 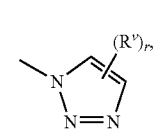 U-48 |
| 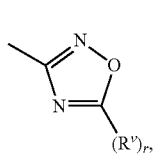 | U-37 | 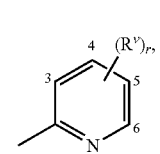 U-49 |

-continued

U-50 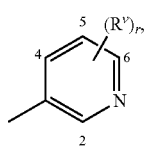

U-51 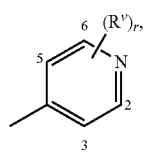

U-52 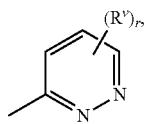

U-53 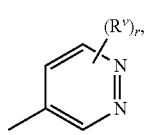

U-54 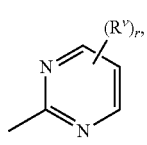

U-55 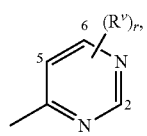

U-56 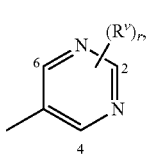

U-57 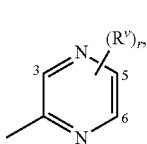

U-58 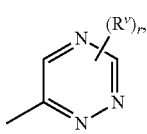

U-59 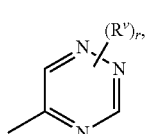

U-60

-continued

U-61 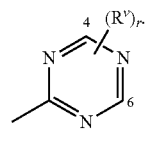

As noted above, Q can be (among others) an 8- to 10-membered aromatic bicyclic ring system optionally substituted with substituents selected from a group of substituents as defined in the Summary of Invention. Examples of optionally substituted 8-, 9- or 10-membered aromatic bicyclic ring systems include the rings U-81 through U-123 illustrated in Exhibit 3 wherein $R^v$ is any substituent as defined in the Summary of the Invention for Q, and r is typically an integer from 0 to 4.

Exhibit 3

U-81 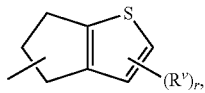

U-82 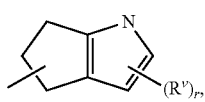

U-83 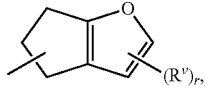

U-84 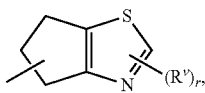

U-85 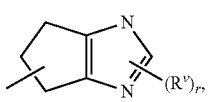

U-86 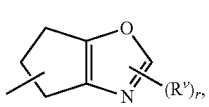

U-87 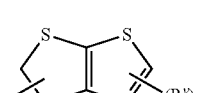

U-89 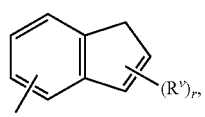

U-90 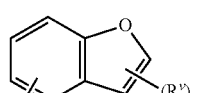

U-91 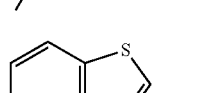

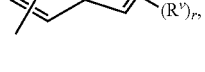

| | | |
|---|---|---|
| 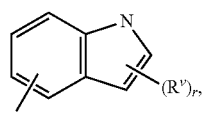 | U-92 | 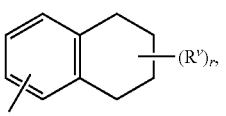 U-106 |
| 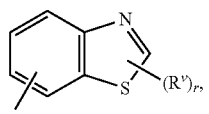 | U-93 | 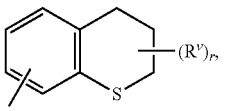 U-107 |
| 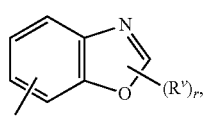 | U-94 | 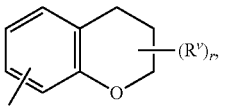 U-108 |
| 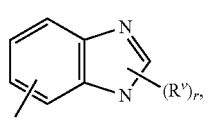 | U-95 | 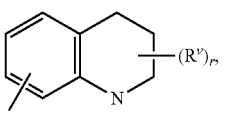 U-109 |
| 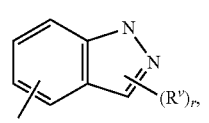 | U-96 | 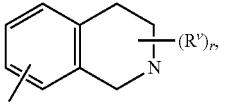 U-110 |
| 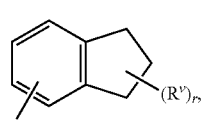 | U-97 | 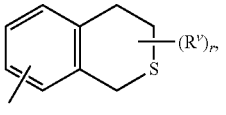 U-111 |
| 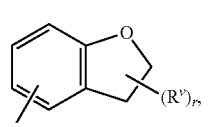 | U-98 | 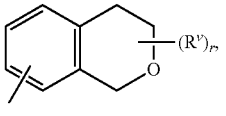 U-112 |
| 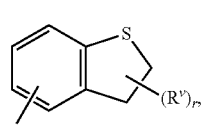 | U-99 | 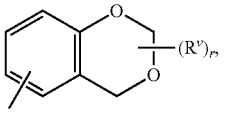 U-113 |
| 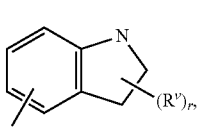 | U-100 | 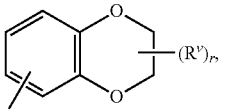 U-114 |
| 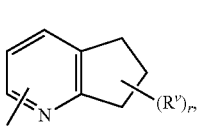 | U-101 | 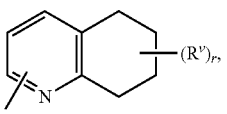 U-115 |
| 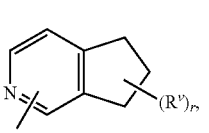 | U-102 | 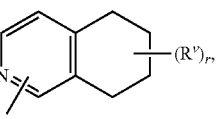 U-116 |
| 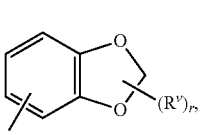 | U-103 | 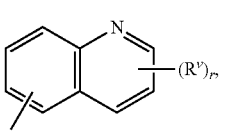 U-117 |
| 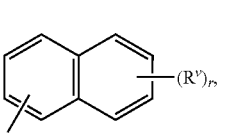 | U-105 | 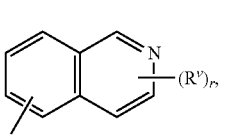 U-118 |

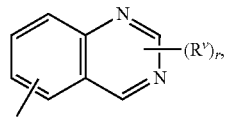
U-119

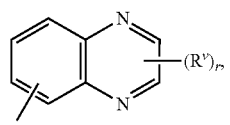
U-120

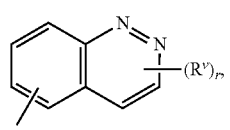
U-121

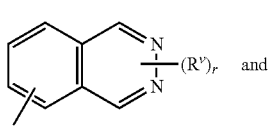
U-122 and

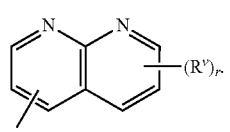
U-123

Although R$^v$ groups are shown in the structures U-1 through U-123, it is noted that they do not need to be present since they are optional substituents. The nitrogen atoms that require substitution to fill their valence are substituted with H or R$^v$. Note that when the attachment point between (R$^v$)$_r$ and the U group is illustrated as floating, (R$^v$)$_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 R$^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds selected from Formula 1, (including all stereoisomers, N-oxides, and salts thereof), can exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of parasitic nematodes. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid, phenol or sulfanilamide (i.e. when R$^3$ is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and salts thereof.

Embodiments of the present invention as described in the Summary of the Invention include those described below. In the following Embodiments, Formula 1 includes stereoisomers, N-oxides, and salts thereof, and reference to "a compound of Formula 1" includes the definitions of substituents specified in the Summary of the Invention unless further defined in the Embodiments.

Embodiment 1

A compound of Formula 1 wherein Z is O.

Embodiment 2

A compound of Formula 1 wherein Z is S.

Embodiment 2a

A compound of Formula 1 wherein $A^1$ is N.

Embodiment 2b

A compound of Formula 1 wherein $A^2$ is N.

Embodiment 2c

A compound of Formula 1 wherein $A^3$ is N.

Embodiment 2d

A compound of Formula 1 wherein $A^4$ is N.

Embodiment 3

A compound of Formula 1 or any of Embodiments 1-2d wherein each $R^1$ is independently halogen, cyano, nitro, $OR^4$, $C_1$-$C_6$ alkyl or $C_1$-$C_6$ haloalkyl.

Embodiment 3a

A compound of Embodiment 3 wherein each $R^1$ is independently halogen, $C_1$-$C_6$ haloalkyl or $C_1$-$C_6$ haloalkoxy (i.e. $OR^4$ and $R^4$ is $C_1$-$C_6$ haloalkyl).

Embodiment 3b

A compound of Embodiment 3a wherein each $R^1$ is independently halogen or $C_1$-$C_2$ haloalkyl.

Embodiment 3c

A compound of Embodiment 3b wherein each $R^1$ is independently F, Cl, Br or $CF_3$.

Embodiment 4

A compound of Formula 1 or any of Embodiments 1-3c wherein Q is phenyl or a 5- or 6-membered heteroaromatic ring, each optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(X)NR^{11}R^{12}$, $S(O)_mR^9$, $S(O)NR^{11}R^{12}$, $OC(O)R^{7a}$ and $N(R^{10})C(O)R^{7a}$.

Embodiment 4a

A compound of Embodiment 4 wherein Q is phenyl or a 5- or 6-membered heteroaromatic ring, each optionally substituted with 1 to 3 substituents independently selected from the group consisting of halogen, cyano, $OR^{4a}$, $C_1$-$C_3$ alkyl, $C_1$-$C_3$ haloalkyl and $C(O)R^{7b}$;
  each $R^{4a}$ is independently $C_1$-$C_3$ alkyl or $C_1$-$C_3$ haloalkyl; and
  each $R^{7b}$ is independently $C_1$-$C_3$ alkyl.

Embodiment 4b

A compound of Embodiment 4 wherein Q is phenyl, pyridinyl, pyrazolyl, oxazolyl, thiazolyl, isoxazolyl, isothiazolyl, furanyl or thienyl, each optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(X)NR^{11}R^{12}$, $S(O)_mR^9$, $S(O)_2NR^{11}R^{12}$, $OC(O)R^{7a}$ and $N(R^{10})C(O)R^{7a}$.

Embodiment 4c

A compound of Embodiment 4b wherein Q is phenyl, pyridinyl, pyrazolyl, oxazolyl, thiazolyl, isoxazolyl, isothiazolyl, furanyl or thienyl, each optionally substituted with 1 to 3 substituents independently selected from the group consisting of halogen, cyano, $OR^{4a}$, $C_1$-$C_3$ alkyl and $C_1$-$C_3$ haloalkyl; and
  each $R^{4a}$ is independently $C_1$-$C_3$ alkyl or $C_1$-$C_3$ haloalkyl.

Embodiment 4d

A compound of Embodiment 4b wherein Q is phenyl optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4e

A compound of Embodiment 4d wherein Q is phenyl optionally substituted with 1 to 3 substituents independently selected from the group consisting of halogen, cyano, $OR^{4a}$, $C_1$-$C_3$ alkyl, $C_1$-$C_3$ haloalkyl and $C(O)R^{7b}$;
  each $R^{4a}$ is independently $C_1$-$C_3$ alkyl or $C_1$-$C_3$ haloalkyl; and
  each $R^{7b}$ is independently $C_1$-$C_3$ alkyl.

Embodiment 4f

A compound of Embodiment 4b wherein Q is pyridinyl optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4g

A compound of Embodiment 4f wherein Q is pyridinyl optionally substituted with 1 to 3 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4h

A compound of Embodiment 4b wherein Q is pyrazolyl optionally substituted with 1 or 2 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4i

A compound of Embodiment 4h wherein Q is pyrazolyl optionally substituted with 1 or 2 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4j

A compound of Embodiment 4b wherein Q is oxazolyl optionally substituted with 1 or 2 substituents independently selected from the group consisting of halogen, cyano, nitro, $OR^4$, $NR^5R^6$, $C_1$-$C_4$ alkyl, $C_1$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)NR^{11}R^{12}$, $OC(O)R^{7a}$ and $N(R^{10})C(O)R^{7a}$.

Embodiment 4k

A compound of Embodiment 4j wherein Q is oxazolyl optionally substituted with 1 or 2 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4l

A compound of Embodiment 4b wherein Q is thiazolyl optionally substituted with 1 or 2 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4m

A compound of Embodiment 4l wherein Q is thiazolyl optionally substituted with 1 or 2 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4n

A compound of Embodiment 4b wherein Q is isoxazolyl optionally substituted with 1 or 2 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4o

A compound of Embodiment 4n wherein Q is isoxazolyl optionally substituted with 1 or 2 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4p

A compound of Embodiment 4b wherein Q is isothiazolyl optionally substituted with 1 or 2 substituents independently selected from the group consisting of halogen, cyano, nitro, $OR^4$, $NR^5R^6$, $C_1$-$C_4$ alkyl, $C_1$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4q

A compound of Embodiment 4p wherein Q is isothiazolyl optionally substituted with 1 or 2 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4r

A compound of Embodiment 4b wherein Q is furanyl optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4s

A compound of Embodiment 4r wherein Q is furanyl optionally substituted with 1 to 3 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4t

A compound of Embodiment 4b wherein Q is thienyl optionally substituted with 1 to 3 substituents independently selected from the group consisting of halogen, cyano, nitro, $OR^4$, $NR^5R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$.

Embodiment 4u

A compound of Embodiment 4t wherein Q is thienyl optionally substituted with 1 to 3 substituents independently selected from the group consisting of halogen, cyano, $OR^{4a}$, $C_1$-$C_3$ alkyl and $C_1$-$C_3$ haloalkyl; and each $R^{4a}$ is independently $C_1$-$C_3$ alkyl or $C_1$-$C_3$ haloalkyl.

Embodiment 4v

A compound of Embodiment 4b wherein Q is phenyl optionally substituted with 1 to 3 substituents independently selected from the group consisting of halogen, cyano, $OR^4$, $NR^5R^6$, $C_1$-$C_4$ alkyl, $C_1$-$C_4$ haloalkyl, $C(X)R^7$ and $C(O)OR^8$.

Embodiment 4w

A compound of Embodiment 4b wherein Q is pyridinyl optionally substituted with 1 to 3 substituents independently selected from the group consisting of halogen, cyano, $OR^4$, $NR^5R^6$, $C_1$-$C_4$ alkyl, $C_1$-$C_4$ haloalkyl, $C(X)R^7$ and $C(O)OR^8$.

Embodiment 4x

A compound of Embodiment 4b wherein Q is furanyl optionally substituted with 1 to 3 substituents independently selected from the group consisting of halogen, cyano, $OR^4$, $NR^5R^6$, $C_1$-$C_4$ alkyl, $C_1$-$C_4$ haloalkyl, $C(X)R^7$ and $C(O)OR^8$.

Embodiment 5

A compound of Formula 1 or any of Embodiments 1-4x wherein $R^2$ is H, halogen or $C_1$-$C_6$ alkyl.

Embodiment 5a

A compound of Embodiment 5 wherein $R^2$ is H, F, Cl, Br or $C_1$-$C_2$ alkyl.

Embodiment 5b

A compound of Embodiment 5a wherein $R^2$ is H, Cl, Br or $CH_3$.

Embodiment 5c

A compound of Embodiment 5a wherein $R^2$ is H.

Embodiment 6

A compound of Formula 1 or any of Embodiments 1-5c wherein $R^3$ is H, $C_1$-$C_6$ alkyl, $C_1$-$C_6$ haloalkyl, $C(X)R^7$, $C(O)OR^8$ or $S(O)_mR^9$; or $C_1$-$C_6$ alkyl substituted with 1 or 2 $OR^4$.

Embodiment 6a

A compound of Embodiment 6 wherein $R^3$ is H or $C_1$-$C_6$ alkyl.

Embodiment 6b

A compound of Embodiment 6a wherein $R^3$ is H.

Embodiment 7

A compound of Formula 1 or any of Embodiments 1-6b wherein $R^4$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_1$-$C_6$ alkyl, $C_2$-$C_6$ alkenyl or $C_2$-$C_6$ alkynyl, each substituted with 1 to 4 substituents independently selected from the group consisting of halogen, cyano, nitro, $OR^{4a}$, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^{7a}$, $C(O)OR^{8a}$, $C(O)NR^{11}R^{12}$, $S(O)_mR^{9a}$ and $S(O)_2NR^{11}R^{12}$.

Embodiment 8

A compound of Formula 1 or any of Embodiments 1-7 wherein $R^5$ is H, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(O)NR^{11}R^{12}$, $S(O)_mR^9$ or $S(O)_2NR^{11}R^{12}$; or $C_3$-$C_7$ cycloalkyl, $C_4$-$C_5$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$.

Embodiment 9

A compound of Formula 1 or any of Embodiments 1-8 wherein $R^6$ is H, $C_1$-$C_6$ alkyl, $C_1$-$C_6$ haloalkyl, $C_2$-$C_6$ alkenyl or $C_2$-$C_6$ alkynyl; or $C_3$-$C_7$ cycloalkyl or $C_1$-$C_4$ cycloalkylalkyl, each optionally substituted with 1 or 2 substituents independently selected from the group consisting of halogen, cyano, $C_1$-$C_4$ alkyl, $C_1$-$C_4$ haloalkyl and $OR^{4a}$;

Embodiment 10

A compound of Formula 1 or any of Embodiments 1-9 wherein $R^7$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$.

Embodiment 11

A compound of Formula 1 or any of Embodiments 1-10 wherein $R^8$ is H, $C_6$-$C_6$ alkyl, $C_1$-$C_4$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_mR^{9a}$; or $C_1$-$C_6$ alkyl substituted with 1 to 4 substituents independently selected from the group consisting of halogen, cyano, nitro, $OR^{4a}$, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^{7a}$, $C(O)OR^{8a}$, $C(O)NR^{11}R^{12}$, $S(O)_mR^{9a}$ and $S(O)_2NR^{11}R^{12}$.

Embodiment 12

A compound of Formula 1 or any of Embodiments 1-11 wherein $R^9$ is H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_2$-$C_6$ alkyl substituted with 1 to 4 substituents independently selected from the group consisting of halogen, cyano, nitro, $OR^{4a}$, $NR^{5a}R^{6a}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^{7a}$, $C(O)OR^{8a}$, $C(O)NR^{11}R^{12}$, $S(O)_mR^{9a}$ and $S(O)_2NR^{11}R^{12}$.

Embodiment 13

A compound of Formula 1 or any of Embodiments 1-12 wherein $R^{10}$ is H, $C_1$-$C_6$ alkyl, $C_1$-$C_6$ haloalkyl, $C_2$-$C_6$ alkenyl or $C_2$-$C_6$ alkynyl.

Embodiment 14

A compound of Formula 1 or any of Embodiments 1-13 wherein $R^{14}$ is $C_3$-$C_7$ cycloalkyl, $C_4$-$C_8$ cycloalkylalkyl or $C_2$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or $C_1$-$C_6$ alkyl substituted with 1 to 4 substituents independently selected from the group consisting of halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(O)NR^{11}R^{12}$, $S(O)_m R^9$ and $S(O)_2 NR^{11}R^{12}$.

Embodiments of this invention, including Embodiments 1-14 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-14 above as well as any other embodiments described herein, and any combination thereof, pertain to the compositions and methods of the present invention.

Combinations of Embodiments 1-14 are illustrated by:

Embodiment A1

A compound of Formula 1 wherein
Z is O; and
Q is phenyl or a 5- or 6-membered heteroaromatic ring, each optionally substituted with 1 to 3 substituents independently selected from the group consisting of halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(X)NR^{11}R^{12}$, $S(O)_m R^9$, $S(O)_2 NR^{11}R^{12}$, $OC(O)R^7$ and $N(R^{10})C(O)R^7$.

Embodiment A2

A compound of Embodiment A1 wherein
Q is phenyl, pyridinyl, pyrazolyl, oxazolyl, thiazolyl, isoxazolyl, isothiazolyl, furanyl or thienyl, each optionally substituted with 1 to 3 substituents independently selected from the group consisting of halogen, cyano, nitro, $OR^4$, $NR^5R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(X)NR^{11}R^{12}$, $S(O)_m R^9$, $S(O)_2 NR^{11}R^{12}$, $OC(O)R^7$ and $N(R^{10})C(O)R^7$.

Embodiment A3

A compound of Embodiment A2 wherein
each $R^1$ is independently halogen, cyano, nitro, $OR^4$, $C_1$-$C_6$ alkyl or $C_1$-$C_6$ haloalkyl;
$R^2$ is H, halogen or $C_1$-$C_6$ alkyl; and
$R^3$ is H, $C(X)R^7$, $C(O)OR^8$ or $S(O)_m R^9$; or $C_1$-$C_6$ alkyl optionally substituted with 1 to 4 substituents independently selected from halogen.

Specific embodiments include compounds of Formula 1 selected from the group consisting of:
N-[(2-chloro-5-methoxyphenyl)sulfonyl]-6-(trifluoromethyl)imidazo[1,2-a]pyrazine-2-carboxamide;
6-bromo-N-[[2-chloro-5-(trifluoromethyl)phenyl]sulfonyl] imidazo[1,2-a]pyrimidine-2-carboxamide; and
N-[[2-chloro-5-(trifluoromethyl)phenyl]sulfonyl]-6-(trifluoromethyl)imidazo[1,2-a]pyrimidine-2-carboxamide.

Of note is that compounds of this invention are characterized by favorable metabolic and/or soil residual patterns and exhibit activity controlling a spectrum of agronomic and nonagronomic parasitic nematodes.

Of particular note, for reasons of parasitic nematode control spectrum and economic importance, protection of agronomic crops from damage or injury caused by parasitic nematodes by controlling parasitic nematodes are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling a parasitic nematode comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent. Embodiments of the invention further include methods for controlling a parasitic nematode comprising contacting the parasitic nematode or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling a parasitic nematode comprising contacting the soil with a liquid composition as a soil drench comprising a biologically effective amount of a compound of any of the preceding Embodiments.

Embodiments of the invention also include a spray composition for controlling a parasitic nematode comprising a biologically effective amount of a compound of any of the preceding Embodiments and a propellant. Embodiments of the invention further include a bait composition for controlling a parasitic nematode comprising a biologically effective amount of a compound of any of the preceding Embodiments, one or more food materials, optionally an attractant, and optionally a humectant.

Embodiments of the invention also include methods for protecting a seed from a parasitic nematode comprising contacting the seed with a biologically effective amount of a compound of any of the preceding Embodiments.

Embodiments of the invention also include methods for controlling a parasitic nematode comprising contacting the parasitic nematode or its environment with a biologically effective amount of a compound of Formula 1, an N-oxide, or a salt thereof, (e.g., as a composition described herein), provided that the methods are not methods of medical treatment of a human or animal body by therapy.

This invention also relates to such methods wherein the parasitic nematode or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-8 can be used to prepare the compounds of Formula 1. The definitions of Z, Q, $R^1$, $R^2$ and $R^3$ in the compounds of Formulae 1-10 below are as defined above in the Summary of the invention unless otherwise noted. Formulae 1a-1c are various subsets of Formula 1, Formulae 2a-2d are various subsets of Formula 2, Formulae 4a-4d are various subsets of Formula 4, Formulae 5a-5d are various subsets of Formula 5, Formulae 7a-7d are various subsets of Formula 7, and all substituents for Formulae 1a-1c, 2a-2d, 4a-4-d, 5a-5d and 7a-7d are as defined above for Formulae 1, 2, 4, 5 and 7, respectively, unless otherwise noted. Room temperature is between about 20 and 25° C.

Compounds of Formula 1a (i.e. Formula 1 wherein Z is oxygen and $R^3$ is H) can be prepared by the reaction of carboxylic acids of Formula 2 with aryl or heteroaryl sulfonamides of Formula 3 as shown in Scheme 1. Typically, an amide coupling reagent and a catalyst such as N,N-dimethylaminopyridine (DMAP) are used. Amide coupling reagents include 1-ethyl-3-(3-dimethylaminopropyl)carbodiimide hydrochloride (EDC), N,N'-dicyclohexylcarbodiimide (DCC) and 1,1'-carbonyldiimidazole (CDI). The reaction can be carried out at temperatures ranging from room temperature to the reflux temperature of the solvent. Typical solvents include alcohols, ethers, esters, amides and halogenated hydrocarbons. Synthesis Example 1 and Step C of Synthesis Example 3 describe a particularly useful set of conditions utilizing EDC/DMAP in a solvent mixture of t-butanol and dichloromethane.

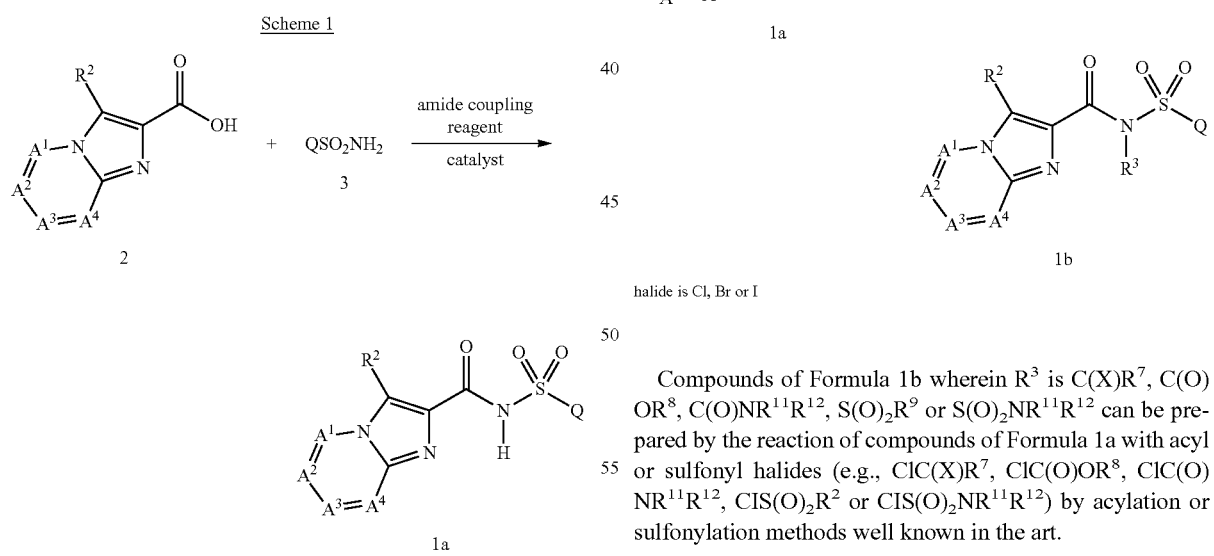

halide is Cl, Br or I

Compounds of Formula 1a can also be prepared by the reaction of carboxylic acid chlorides of Formula 4 with aryl or heteroaryl sulfonamides of Formula 3 as shown in Scheme 2. The reaction typically involves use of a base such as a trialkylamine or pyridine and optionally a catalyst such as DMAP in the presence of a solvent. The reaction can be carried out at temperatures ranging from room temperature to the reflux temperature of the solvent. Typical solvents include acetonitrile, tetrahydrofuran, diethyl ether, ethyl acetate, toluene, methylene chloride and chloroform.

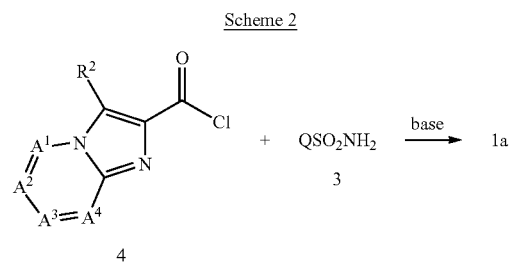

Compounds of Formula 1b wherein $R^3$ is optionally substituted alkyl, alkenyl, alkynyl or cycloalkyl can be prepared by the reaction of compounds of Formula 1a with appropriately substituted alkyl, alkenyl, alkynyl or cycloalkyl halides and base as shown in Scheme 3. Typical reaction conditions include potassium carbonate as the base and N,N-dimethylformamide (DMF) as the solvent at temperatures ranging from room temperature to 100° C.

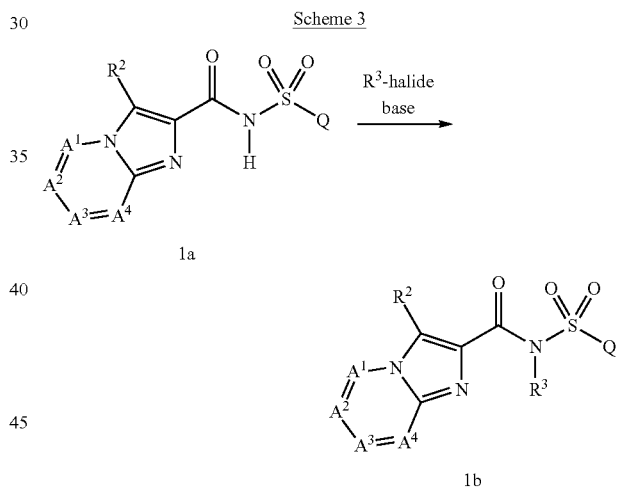

Compounds of Formula 1b wherein $R^3$ is $C(X)R^7$, $C(O)OR^8$, $C(O)NR^{11}R^{12}$, $S(O)_2R^9$ or $S(O)_2NR^{11}R^{12}$ can be prepared by the reaction of compounds of Formula 1a with acyl or sulfonyl halides (e.g., $ClC(X)R^7$, $ClC(O)OR^8$, $ClC(O)NR^{11}R^{12}$, $ClS(O)_2R^2$ or $ClS(O)_2NR^{11}R^{12}$) by acylation or sulfonylation methods well known in the art.

Compounds of Formula 1b wherein $R^3$ is optionally substituted alkyl, alkenyl, alkynyl, cycloalkyl or phenyl can be prepared by the reaction of acid chlorides of Formula 4 with sulfonamides of Formula 9 as shown in Scheme 4. Alternatively, compounds of Formula 1b wherein $R^3$ is optionally substituted alkyl, alkenyl, alkynyl, cycloalkyl or phenyl can be prepared by the reaction of carboxylic acids of Formula 2 with sulfonamides of Formula 9 by the method of Scheme 1.

Scheme 4

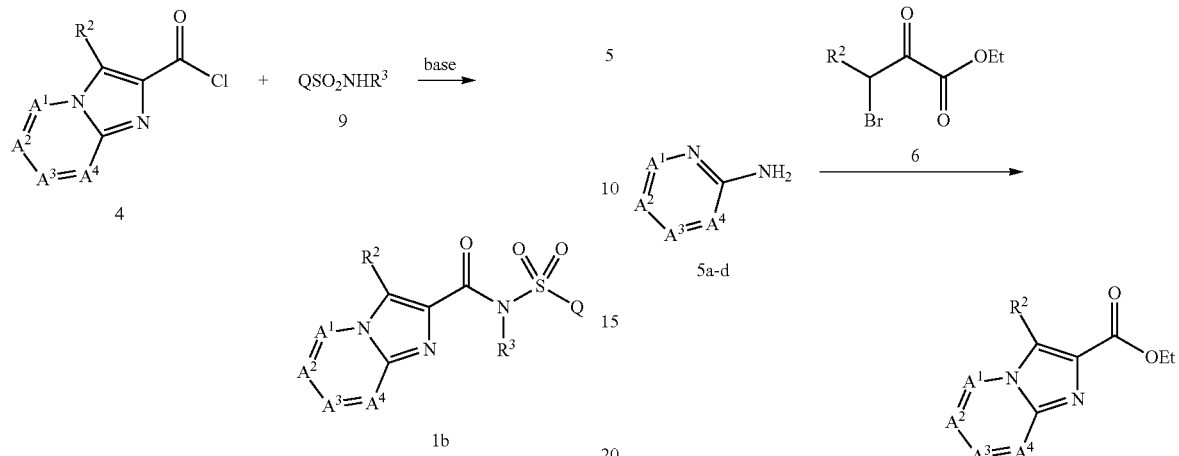

$R^3$ is optionally substituted alkyl, alkenyl, alkynyl, cycloalkyl or phenyl

Thioamides of Formula 1c (i.e. Formula 1 wherein Z is sulfur) can be prepared by the reaction of compounds of Formula 1b (i.e. Formula 1 wherein X is O) with thiation reagents such as phosphorus pentasulfide or Lawesson's reagent as depicted in Scheme 5.

Scheme 5

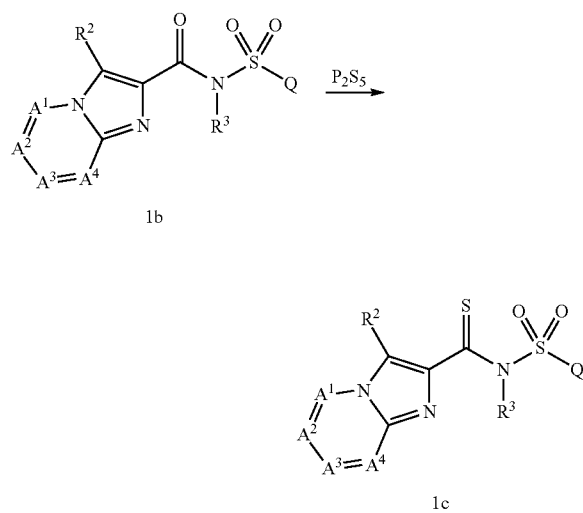

Carboxylic acids of Formulae 2a-d and acid chlorides of Formulae 4a-d can be prepared by the methods shown in Scheme 6. Reaction of suitably substituted 2-aminodiazines of Formulae 5a-d with 2-bromopyruvates of Formula 6 (wherein $R^2$ is H, optionally substituted alkyl, alkenyl, alkynyl, $C(O)R^7$, $C(O)OR^8$ or $C(O)NR^{11}R^{12}$, or an optionally substituted phenyl, naphthalenyl or a 5- or 6-membered heteroaromatic ring) at temperatures ranging from room temperature to the boiling temperature of the solvent affords the carboxylic esters of Formulae 7a-d.

Scheme 6

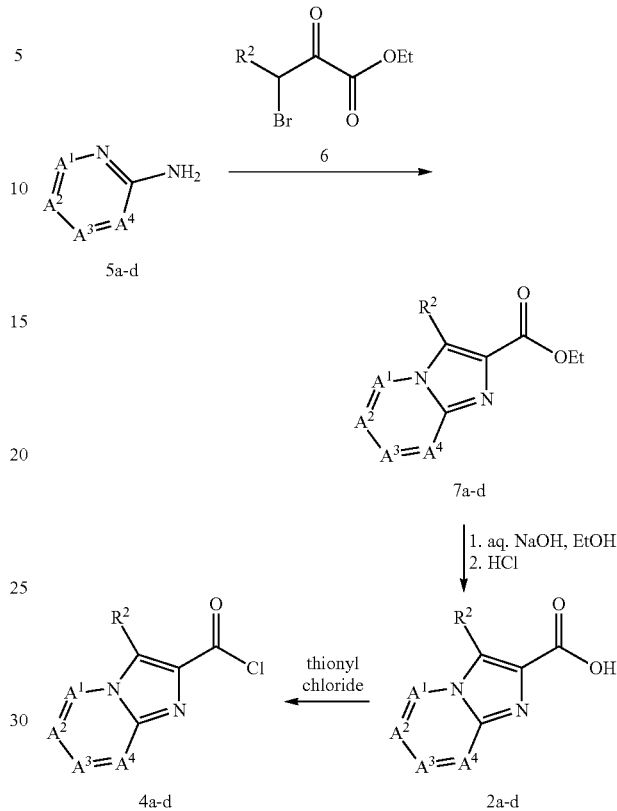

For compounds of Formulae 2a, 4a, 5a and 7a: $A^4$ is N, and $A^1$, $A^2$ and $A^3$ are $CR^1$
For compounds of Formulae 2b, 4b, 5b and 7b: $A^3$ is N, and $A^1$, $A^2$ and $A^4$ are $CR^1$
For compounds of Formulae 2c, 4c, 5c and 7c: $A^2$ is N, and $A^1$, $A^3$ and $A^4$ are $CR^1$
For compounds of Formulae 2d, 4d, 5d and 7d: $A^1$ is N, and $A^2$, $A^3$ and $A^4$ are $CR^1$ Treatment of esters of Formulae 7a-d with aqueous hydroxide base such as sodium hydroxide, and a water-miscible solvent such as ethanol, followed by acidification with acids such as hydrochloric acid, results in hydrolysis to the carboxylic acids of Formula 2a-d. The carboxylic acids of Formula 2a-d can be converted to the acid chlorides of Formula 4a-d by well known conventional means such as treatment with thionyl chloride or oxalyl chloride and a catalytic amount of N,N-dimethylformamide (DMF) in moderately polar, aprotic solvents including dichloromethane, dichloroethane, toluene and ethyl acetate.

Bromopyruvates of Formula 6 are commercially available or can be prepared by a variety of well-known synthetic methods, including the bromination of optionally substituted pyruvates or lactates (alpha-hydroxy esters), Typical reaction conditions include direct bromination with bromine (see, for example, *JACS* 1944, 66, 1656-1659) or $CuBr_2$ in ethyl acetate/chloroform (see, for example, *JOC* 2002, 67(4), 1102-1108), or reaction of a lactate with N-bromosuccinimide in $CCl_4$ (see, for example, *JACS* 1954, 76, 5796-5797), Bromopyruvates of Formula 6 wherein $R^2$ is other than H can also be prepared by methods known in the art (e.g., electrophilic methods such as bromination or nitration to introduce bromine or a nitro group, respectively, and further elaboration of these substituents as appropriate).

Representative procedures for the preparation of compounds of Formula 7a are disclosed in the following references: *Organic Letters* 2010, 12(3), 412-415; *Journal of*

Combinatorial Chemistry 2006, 8(5), 659-663; European Journal of Medicinal Chemistry 1991, 26(1), 13-18; and J Med. Chem. 1991, 34, 2020-2067.

Representative procedures for the preparation of compounds of Formula 7b are disclosed in the following references: European Journal of Medicinal Chemistry 1983, 18(5), 413-417; and Farmaco, Edizione Scientifica 1981, 36(1), 61-80.

Representative procedures for the preparation of compounds of Formula 7e are disclosed in the following references: Bioorganic and Medicinal Chemistry 2009, 17(13), 4448-4458; and Farmaco, Edizione Scientifica 1980, 35(8), 654-673.

Representative procedures for the preparation of compounds of Formula 7d are disclosed in the following references: J. Het Chem. 2002, 39(4), 737-742; and J. Het Chem. 1968, 5(1), 35-39.

Alternatively, carboxylic acids of Formulae 2a-d can be prepared directly by the reaction shown in Scheme 7. Reaction of suitably substituted 2-aminodiazines of Formula 5a-d with 2-bromopyruvates of Formula 8 (wherein $R^2$ is H, optionally substituted alkyl, alkenyl, alkynyl, $C(O)R^7$, $C(O)OR^8$ or $C(O)NR^{11}R^{12}$, or an optionally substituted phenyl, naphthalenyl or a 5- or 6-membered heteroaromatic ring) at temperatures ranging from room temperature to the boiling temperature of the solvent affords the carboxylic acids of Formulae 2a-d, which can be initially isolated as hydrobromide salts.

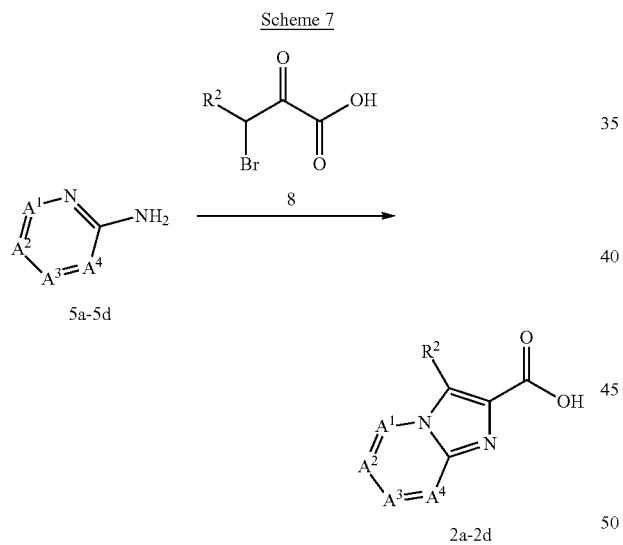

Many sulfonamides of Formulae 3 and 9 are known in the chemical literature or are available commercially. As shown in Scheme 8, sulfonamides of Formula 3 are readily prepared from the corresponding sulfonyl chlorides of Formula 10 by reaction with ammonia, while sulfonamides of Formula 9 are readily prepared from the corresponding sulfonyl chlorides of Formula 10 by reaction with $R^3NH_2$. The sulfonyl chloride intermediates are available commercially or can be prepared by a large variety of methods known in the literature. Three of the most common methods of preparation are shown in Scheme 8, including (a) direct chlorosulfonylation of aromatic and heteroaromatic systems with chlorosulfonic acid, (b) oxidation of sulfides (for example with sodium hypochlorite) in the presence of hydrochloric acid, and (c) diazotization and chlorosulfonylation of aromatic and heteroaromatic amines. These three methods are meant only to be illustrative; a large variety of other synthetic methods are available for the preparation of sulfonyl chlorides and sulfonamides.

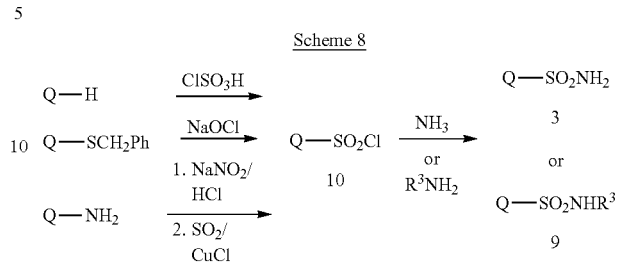

Examples of intermediates useful in the preparation of compounds of this invention are shown in Tables I-1 through I-4. The following abbreviations are used in the Tables which follow: Me means methyl, Et means ethyl, i-Pr means isopropyl, n-Pr means normal propyl, Ome means methoxy and SMe means thiomethoxy.

TABLE I-1

| $R^{1c}$ is H | | | |
|---|---|---|---|
| $R^{1b}$ | $R^{1d}$ | $R^2$ | L |
| H | H | H | Cl |
| H | H | H | OH |
| H | H | H | $OCH_2CH_3$ |
| H | H | $CH_3$ | Cl |
| H | H | $CH_3$ | OH |
| H | H | $CH_3$ | $OCH_2CH_3$ |
| H | H | Cl | Cl |
| H | H | Cl | OH |
| H | H | Cl | $OCH_2CH_3$ |
| H | H | Br | Cl |
| H | H | Br | OH |
| H | H | Br | $OCH_2CH_3$ |
| H | F | H | Cl |
| H | F | H | OH |
| H | F | H | $OCH_2CH_3$ |
| H | F | $CH_3$ | Cl |
| H | F | $CH_3$ | OH |
| H | F | $CH_3$ | $OCH_2CH_3$ |
| H | F | Cl | Cl |
| H | F | Cl | OH |
| H | F | Cl | $OCH_2CH_3$ |
| H | F | Br | Cl |
| H | F | Br | OH |
| H | F | Br | $OCH_2CH_3$ |
| H | Cl | H | Cl |
| H | Cl | H | OH |
| H | Cl | H | $OCH_2CH_3$ |
| H | Cl | $CH_3$ | Cl |
| H | Cl | $CH_3$ | OH |
| H | Cl | $CH_3$ | $OCH_2CH_3$ |
| H | Cl | Cl | Cl |
| H | Cl | Cl | OH |
| H | Cl | Cl | $OCH_2CH_3$ |
| H | Cl | Br | Cl |
| H | Cl | Br | OH |
| H | Cl | Br | $OCH_2CH_3$ |

TABLE I-1-continued

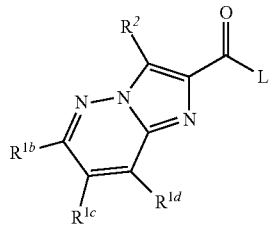

R$^{1c}$ is H

| R$^{1b}$ | R$^{1d}$ | R$^2$ | L |
|---|---|---|---|
| H | Br | H | Cl |
| H | Br | H | OH |
| H | Br | H | OCH$_2$CH$_3$ |
| H | Br | CH$_3$ | Cl |
| H | Br | CH$_3$ | OH |
| H | Br | CH$_3$ | OCH$_2$CH$_3$ |
| H | Br | Cl | Cl |
| H | Br | Cl | OH |
| H | Br | Cl | OCH$_2$CH$_3$ |
| H | Br | Br | Cl |
| H | Br | Br | OH |
| H | Br | Br | OCH$_2$CH$_3$ |
| Cl | H | H | Cl |
| Cl | H | H | OH |
| Cl | H | H | OCH$_2$CH$_3$ |
| Cl | H | CH$_3$ | Cl |
| Cl | H | CH$_3$ | OH |
| Cl | H | CH$_3$ | OCH$_2$CH$_3$ |
| Cl | H | Cl | Cl |
| Cl | H | Cl | OH |
| Cl | H | Cl | OCH$_2$CH$_3$ |
| Cl | H | Br | Cl |
| Cl | H | Br | OH |
| Cl | H | Br | OCH$_2$CH$_3$ |
| Cl | F | H | Cl |
| Cl | F | H | OH |
| Cl | F | H | OCH$_2$CH$_3$ |
| Cl | F | CH$_3$ | Cl |
| Cl | F | CH$_3$ | OH |
| Cl | F | CH$_3$ | OCH$_2$CH$_3$ |
| Cl | F | Cl | Cl |
| Cl | F | Cl | OH |
| Cl | F | Cl | OCH$_2$CH$_3$ |
| Cl | F | Br | Cl |
| Cl | F | Br | OH |
| Cl | F | Br | OCH$_2$CH$_3$ |
| Cl | Cl | H | Cl |
| Cl | Cl | H | OH |
| Cl | Cl | H | OCH$_2$CH$_3$ |
| Cl | Cl | CH$_3$ | Cl |
| Cl | Cl | CH$_3$ | OH |
| Cl | Cl | CH$_3$ | OCH$_2$CH$_3$ |
| Cl | Cl | Cl | Cl |
| Cl | Cl | Cl | OH |
| Cl | Cl | Cl | OCH$_2$CH$_3$ |
| Cl | Cl | Br | Cl |
| Cl | Cl | Br | OH |
| Cl | Cl | Br | OCH$_2$CH$_3$ |
| Cl | Br | H | Cl |
| Cl | Br | H | OH |
| Cl | Br | H | OCH$_2$CH$_3$ |
| Cl | Br | CH$_3$ | Cl |
| Cl | Br | CH$_3$ | OH |
| Cl | Br | CH$_3$ | OCH$_2$CH$_3$ |
| Cl | Br | Cl | Cl |
| Cl | Br | Cl | OH |
| Cl | Br | Cl | OCH$_2$CH$_3$ |
| Cl | Br | Br | Cl |
| Cl | Br | Br | OH |
| Cl | Br | Br | OCH$_2$CH$_3$ |
| CF$_3$ | H | H | Cl |
| CF$_3$ | H | H | OH |
| CF$_3$ | H | H | OCH$_2$CH$_3$ |
| CF$_3$ | H | CH$_3$ | Cl |
| CF$_3$ | H | CH$_3$ | OH |
| CF$_3$ | H | CH$_3$ | OCH$_2$CH$_3$ |
| CF$_3$ | H | Cl | Cl |
| CF$_3$ | H | Cl | OH |
| CF$_3$ | H | Cl | OCH$_2$CH$_3$ |
| CF$_3$ | H | Br | Cl |
| CF$_3$ | H | Br | OH |
| CF$_3$ | H | Br | OCH$_2$CH$_3$ |
| CF$_3$ | F | H | Cl |
| CF$_3$ | F | H | OH |
| CF$_3$ | F | H | OCH$_2$CH$_3$ |
| CF$_3$ | F | CH$_3$ | Cl |
| CF$_3$ | F | CH$_3$ | OH |
| CF$_3$ | F | CH$_3$ | OCH$_2$CH$_3$ |
| CF$_3$ | F | Cl | Cl |
| CF$_3$ | F | Cl | OH |
| CF$_3$ | F | Cl | OCH$_2$CH$_3$ |
| CF$_3$ | F | Br | Cl |
| CF$_3$ | F | Br | OH |
| CF$_3$ | F | Br | OCH$_2$CH$_3$ |
| CF$_3$ | Cl | H | Cl |
| CF$_3$ | Cl | H | OH |
| CF$_3$ | Cl | H | OCH$_2$CH$_3$ |
| CF$_3$ | Cl | CH$_3$ | Cl |
| CF$_3$ | Cl | CH$_3$ | OH |
| CF$_3$ | Cl | CH$_3$ | OCH$_2$CH$_3$ |
| CF$_3$ | Cl | Cl | Cl |
| CF$_3$ | Cl | Cl | OH |
| CF$_3$ | Cl | Cl | OCH$_2$CH$_3$ |
| CF$_3$ | Cl | Br | Cl |
| CF$_3$ | Cl | Br | OH |
| CF$_3$ | Cl | Br | OCH$_2$CH$_3$ |
| CF$_3$ | Br | H | Cl |
| CF$_3$ | Br | H | OH |
| CF$_3$ | Br | H | OCH$_2$CH$_3$ |
| CF$_3$ | Br | CH$_3$ | Cl |
| CF$_3$ | Br | CH$_3$ | OH |
| CF$_3$ | Br | CH$_3$ | OCH$_2$CH$_3$ |
| CF$_3$ | Br | Cl | Cl |
| CF$_3$ | Br | Cl | OH |
| CF$_3$ | Br | Cl | OCH$_2$CH$_3$ |
| CF$_3$ | Br | Br | Cl |
| CF$_3$ | Br | Br | OH |
| CF$_3$ | Br | Br | OCH$_2$CH$_3$ |
| Br | H | H | Cl |
| Br | H | H | OH |
| Br | H | H | OCH$_2$CH$_3$ |
| Br | H | CH$_3$ | Cl |
| Br | H | CH$_3$ | OH |
| Br | H | CH$_3$ | OCH$_2$CH$_3$ |
| Br | H | Cl | Cl |
| Br | H | Cl | OH |
| Br | H | Cl | OCH$_2$CH$_3$ |
| Br | H | Br | Cl |
| Br | H | Br | OH |
| Br | H | Br | OCH$_2$CH$_3$ |
| Br | F | H | Cl |
| Br | F | H | OH |
| Br | F | H | OCH$_2$CH$_3$ |
| Br | F | CH$_3$ | Cl |
| Br | F | CH$_3$ | OH |
| Br | F | CH$_3$ | OCH$_2$CH$_3$ |
| Br | F | Cl | Cl |
| Br | F | Cl | OH |

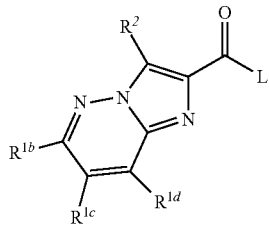

TABLE I-1-continued

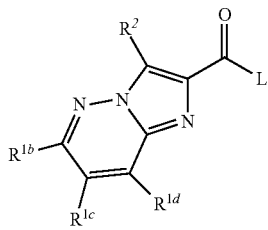

R$^{1c}$ is H

| R$^{1b}$ | R$^{1d}$ | R$^{2}$ | L |
|---|---|---|---|
| Br | F | Cl | OCH$_2$CH$_3$ |
| Br | F | Br | Cl |
| Br | F | Br | OH |
| Br | F | Br | OCH$_2$CH$_3$ |
| Br | Cl | H | Cl |
| Br | Cl | H | OH |
| Br | Cl | H | OCH$_2$CH$_3$ |
| Br | Cl | CH$_3$ | Cl |
| Br | Cl | CH$_3$ | OH |
| Br | Cl | CH$_3$ | OCH$_2$CH$_3$ |
| Br | Cl | Cl | Cl |
| Br | Cl | Cl | OH |
| Br | Cl | Cl | OCH$_2$CH$_3$ |
| Br | Cl | Br | Cl |
| Br | Cl | Br | OH |
| Br | Cl | Br | OCH$_2$CH$_3$ |
| Br | Br | H | Cl |
| Br | Br | H | OH |
| Br | Br | H | OCH$_2$CH$_3$ |
| Br | Br | CH$_3$ | Cl |
| Br | Br | CH$_3$ | OH |
| Br | Br | CH$_3$ | OCH$_2$CH$_3$ |
| Br | Br | Cl | Cl |
| Br | Br | Cl | OH |
| Br | Br | Cl | OCH$_2$CH$_3$ |
| Br | Br | Br | Cl |
| Br | Br | Br | OH |
| Br | Br | Br | OCH$_2$CH$_3$ |

TABLE I-2

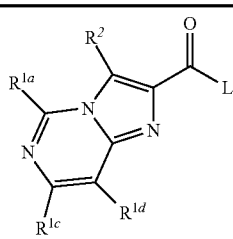

R$^{1a}$ is H; R$^{1d}$ is H

| R$^{1c}$ | R$^{2}$ | L |
|---|---|---|
| H | H | Cl |
| H | H | OH |
| H | H | OCH$_2$CH$_3$ |
| H | CH$_3$ | Cl |
| H | CH$_3$ | OH |
| H | CH$_3$ | OCH$_2$CH$_3$ |
| H | Cl | Cl |
| H | Cl | OH |
| H | Cl | OCH$_2$CH$_3$ |
| H | Br | Cl |
| H | Br | OH |
| H | Br | OCH$_2$CH$_3$ |
| Br | H | Cl |
| Br | H | OH |
| Br | H | OCH$_2$CH$_3$ |

TABLE I-2-continued

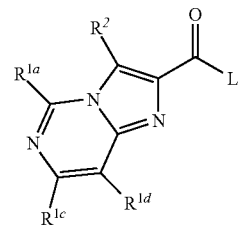

R$^{1a}$ is H; R$^{1d}$ is H

| R$^{1c}$ | R$^{2}$ | L |
|---|---|---|
| Br | CH$_3$ | Cl |
| Br | CH$_3$ | OH |
| Br | CH$_3$ | OCH$_2$CH$_3$ |
| Br | Cl | Cl |
| Br | Cl | OH |
| Br | Cl | OCH$_2$CH$_3$ |
| Br | Br | Cl |
| Br | Br | OH |
| Br | Br | OCH$_2$CH$_3$ |
| Cl | H | Cl |
| Cl | H | OH |
| Cl | H | OCH$_2$CH$_3$ |
| Cl | CH$_3$ | Cl |
| Cl | CH$_3$ | OH |
| Cl | CH$_3$ | OCH$_2$CH$_3$ |
| Cl | Cl | Cl |
| Cl | Cl | OH |
| Cl | Cl | OCH$_2$CH$_3$ |
| Cl | Br | Cl |
| Cl | Br | OH |
| Cl | Br | OCH$_2$CH$_3$ |

TABLE I-3

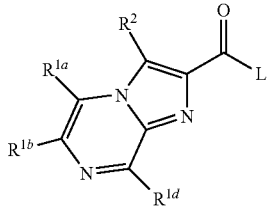

R$^{1a}$ is H

| R$^{1b}$ | R$^{1d}$ | R$^{2}$ | L |
|---|---|---|---|
| H | H | H | Cl |
| H | H | H | OH |
| H | H | H | OCH$_2$CH$_3$ |
| H | H | CH$_3$ | Cl |
| H | H | CH$_3$ | OH |
| H | H | CH$_3$ | OCH$_2$CH$_3$ |
| H | H | Cl | Cl |
| H | H | Cl | OH |
| H | H | Cl | OCH$_2$CH$_3$ |
| H | H | Br | Cl |
| H | H | Br | OH |
| H | H | Br | OCH$_2$CH$_3$ |
| H | F | H | Cl |
| H | F | H | OH |
| H | F | H | OCH$_2$CH$_3$ |
| H | F | CH$_3$ | Cl |
| H | F | CH$_3$ | OH |
| H | F | CH$_3$ | OCH$_2$CH$_3$ |
| H | F | Cl | Cl |
| H | F | Cl | OH |
| H | F | Cl | OCH$_2$CH$_3$ |
| H | F | Br | Cl |
| H | F | Br | OH |

TABLE I-3-continued

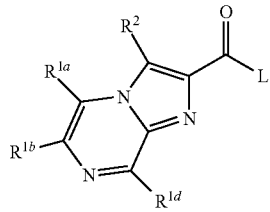

R$^{1a}$ is H

| R$^{1b}$ | R$^{1d}$ | R$^2$ | L |
|---|---|---|---|
| H | F | Br | OCH$_2$CH$_3$ |
| H | Cl | H | Cl |
| H | Cl | H | OH |
| H | Cl | H | OCH$_2$CH$_3$ |
| H | Cl | CH$_3$ | Cl |
| H | Cl | CH$_3$ | OH |
| H | Cl | CH$_3$ | OCH$_2$CH$_3$ |
| H | Cl | Cl | Cl |
| H | Cl | Cl | OH |
| H | Cl | Cl | OCH$_2$CH$_3$ |
| H | Cl | Br | Cl |
| H | Cl | Br | OH |
| H | Cl | Br | OCH$_2$CH$_3$ |
| H | Br | H | Cl |
| H | Br | H | OH |
| H | Br | H | OCH$_2$CH$_3$ |
| H | Br | CH$_3$ | Cl |
| H | Br | CH$_3$ | OH |
| H | Br | CH$_3$ | OCH$_2$CH$_3$ |
| H | Br | Cl | Cl |
| H | Br | Cl | OH |
| H | Br | Cl | OCH$_2$CH$_3$ |
| H | Br | Br | Cl |
| H | Br | Br | OH |
| H | Br | Br | OCH$_2$CH$_3$ |
| Cl | H | H | Cl |
| Cl | H | H | OH |
| Cl | H | H | OCH$_2$CH$_3$ |
| Cl | H | CH$_3$ | Cl |
| Cl | H | CH$_3$ | OH |
| Cl | H | CH$_3$ | OCH$_2$CH$_3$ |
| Cl | H | Cl | Cl |
| Cl | H | Cl | OH |
| Cl | H | Cl | OCH$_2$CH$_3$ |
| Cl | H | Br | Cl |
| Cl | H | Br | OH |
| Cl | H | Br | OCH$_2$CH$_3$ |
| Cl | F | H | Cl |
| Cl | F | H | OH |
| Cl | F | H | OCH$_2$CH$_3$ |
| Cl | F | CH$_3$ | Cl |
| Cl | F | CH$_3$ | OH |
| Cl | F | CH$_3$ | OCH$_2$CH$_3$ |
| Cl | F | Cl | Cl |
| Cl | F | Cl | OH |
| Cl | F | Cl | OCH$_2$CH$_3$ |
| Cl | F | Br | Cl |
| Cl | F | Br | OH |
| Cl | F | Br | OCH$_2$CH$_3$ |
| Cl | Cl | H | Cl |
| Cl | Cl | H | OH |
| Cl | Cl | H | OCH$_2$CH$_3$ |
| Cl | Cl | CH$_3$ | Cl |
| Cl | Cl | CH$_3$ | OH |
| Cl | Cl | CH$_3$ | OCH$_2$CH$_3$ |
| Cl | Cl | Cl | Cl |
| Cl | Cl | Cl | OH |
| Cl | Cl | Cl | OCH$_2$CH$_3$ |
| Cl | Cl | Br | Cl |
| Cl | Cl | Br | OH |
| Cl | Cl | Br | OCH$_2$CH$_3$ |
| Cl | Br | H | Cl |
| Cl | Br | H | OH |
| Cl | Br | H | OCH$_2$CH$_3$ |
| Cl | Br | CH$_3$ | Cl |

TABLE I-3-continued

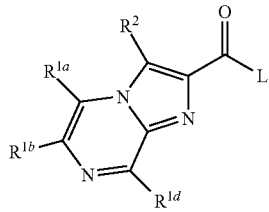

R$^{1a}$ is H

| R$^{1b}$ | R$^{1d}$ | R$^2$ | L |
|---|---|---|---|
| Cl | Br | CH$_3$ | OH |
| Cl | Br | CH$_3$ | OCH$_2$CH$_3$ |
| Cl | Br | Cl | Cl |
| Cl | Br | Cl | OH |
| Cl | Br | Cl | OCH$_2$CH$_3$ |
| Cl | Br | Br | Cl |
| Cl | Br | Br | OH |
| Cl | Br | Br | OCH$_2$CH$_3$ |
| CF$_3$ | H | H | Cl |
| CF$_3$ | H | H | OH |
| CF$_3$ | H | H | OCH$_2$CH$_3$ |
| CF$_3$ | H | CH$_3$ | Cl |
| CF$_3$ | H | CH$_3$ | OH |
| CF$_3$ | H | CH$_3$ | OCH$_2$CH$_3$ |
| CF$_3$ | H | Cl | Cl |
| CF$_3$ | H | Cl | OH |
| CF$_3$ | H | Cl | OCH$_2$CH$_3$ |
| CF$_3$ | H | Br | Cl |
| CF$_3$ | H | Br | OH |
| CF$_3$ | H | Br | OCH$_2$CH$_3$ |
| CF$_3$ | F | H | Cl |
| CF$_3$ | F | H | OH |
| CF$_3$ | F | H | OCH$_2$CH$_3$ |
| CF$_3$ | F | CH$_3$ | Cl |
| CF$_3$ | F | CH$_3$ | OH |
| CF$_3$ | F | CH$_3$ | OCH$_2$CH$_3$ |
| CF$_3$ | F | Cl | Cl |
| CF$_3$ | F | Cl | OH |
| CF$_3$ | F | Cl | OCH$_2$CH$_3$ |
| CF$_3$ | F | Br | Cl |
| CF$_3$ | F | Br | OH |
| CF$_3$ | F | Br | OCH$_2$CH$_3$ |
| CF$_3$ | Cl | H | Cl |
| CF$_3$ | Cl | H | OH |
| CF$_3$ | Cl | H | OCH$_2$CH$_3$ |
| CF$_3$ | Cl | CH$_3$ | Cl |
| CF$_3$ | Cl | CH$_3$ | OH |
| CF$_3$ | Cl | CH$_3$ | OCH$_2$CH$_3$ |
| CF$_3$ | Cl | Cl | Cl |
| CF$_3$ | Cl | Cl | OH |
| CF$_3$ | Cl | Cl | OCH$_2$CH$_3$ |
| CF$_3$ | Cl | Br | Cl |
| CF$_3$ | Cl | Br | OH |
| CF$_3$ | Cl | Br | OCH$_2$CH$_3$ |
| CF$_3$ | Br | H | Cl |
| CF$_3$ | Br | H | OH |
| CF$_3$ | Br | H | OCH$_2$CH$_3$ |
| CF$_3$ | Br | CH$_3$ | Cl |
| CF$_3$ | Br | CH$_3$ | OH |
| CF$_3$ | Br | CH$_3$ | OCH$_2$CH$_3$ |
| CF$_3$ | Br | Cl | Cl |
| CF$_3$ | Br | Cl | OH |
| CF$_3$ | Br | Cl | OCH$_2$CH$_3$ |
| CF$_3$ | Br | Br | Cl |
| CF$_3$ | Br | Br | OH |
| CF$_3$ | Br | Br | OCH$_2$CH$_3$ |
| Br | H | H | Cl |
| Br | H | H | OH |
| Br | H | H | OCH$_2$CH$_3$ |
| Br | H | CH$_3$ | Cl |
| Br | H | CH$_3$ | OH |
| Br | H | CH$_3$ | OCH$_2$CH$_3$ |
| Br | H | Cl | Cl |
| Br | H | Cl | OH |
| Br | H | Cl | OCH$_2$CH$_3$ |

TABLE I-3-continued

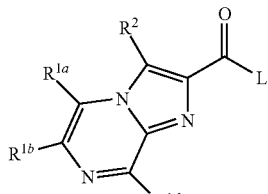

R$^{1a}$ is H

| R$^{1b}$ | R$^{1d}$ | R$^2$ | L |
|---|---|---|---|
| Br | H | Br | Cl |
| Br | H | Br | OH |
| Br | H | Br | OCH$_2$CH$_3$ |
| Br | F | H | Cl |
| Br | F | H | OH |
| Br | F | H | OCH$_2$CH$_3$ |
| Br | F | CH$_3$ | Cl |
| Br | F | CH$_3$ | OH |
| Br | F | CH$_3$ | OCH$_2$CH$_3$ |
| Br | F | Cl | Cl |
| Br | F | Cl | OH |
| Br | F | Cl | OCH$_2$CH$_3$ |
| Br | F | Br | Cl |
| Br | F | Br | OH |
| Br | F | Br | OCH$_2$CH$_3$ |
| Br | Cl | H | Cl |
| Br | Cl | H | OH |
| Br | Cl | H | OCH$_2$CH$_3$ |
| Br | Cl | CH$_3$ | Cl |
| Br | Cl | CH$_3$ | OH |
| Br | Cl | CH$_3$ | OCH$_2$CH$_3$ |
| Br | Cl | Cl | Cl |
| Br | Cl | Cl | OH |
| Br | Cl | Cl | OCH$_2$CH$_3$ |
| Br | Cl | Br | Cl |
| Br | Cl | Br | OH |
| Br | Cl | Br | OCH$_2$CH$_3$ |
| Br | Br | H | Cl |
| Br | Br | H | OH |
| Br | Br | H | OCH$_2$CH$_3$ |
| Br | Br | CH$_3$ | Cl |
| Br | Br | CH$_3$ | OH |
| Br | Br | CH$_3$ | OCH$_2$CH$_3$ |
| Br | Br | Cl | Cl |
| Br | Br | Cl | OH |
| Br | Br | Cl | OCH$_2$CH$_3$ |
| Br | Br | Br | Cl |
| Br | Br | Br | OH |
| Br | Br | Br | OCH$_2$CH$_3$ |

TABLE I-4

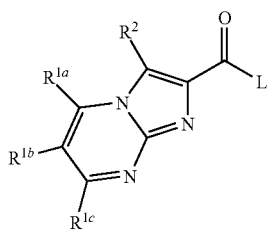

R$^{1a}$ is H; R$^{1c}$ is H

| R$^{1b}$ | R$^2$ | L |
|---|---|---|
| H | H | Cl |
| H | H | OH |
| H | H | OCH$_2$CH$_3$ |
| H | CH$_3$ | Cl |
| H | CH$_3$ | OH |

TABLE I-4-continued

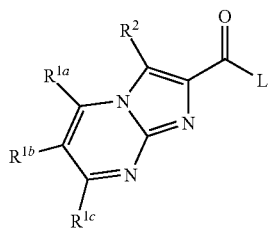

R$^{1a}$ is H; R$^{1c}$ is H

| R$^{1b}$ | R$^2$ | L |
|---|---|---|
| H | CH$_3$ | OCH$_2$CH$_3$ |
| H | Cl | Cl |
| H | Cl | OH |
| H | Cl | OCH$_2$CH$_3$ |
| H | Br | Cl |
| H | Br | OH |
| H | Br | OCH$_2$CH$_3$ |
| Br | H | Cl |
| Br | H | OH |
| Br | H | OCH$_2$CH$_3$ |
| Br | CH$_3$ | Cl |
| Br | CH$_3$ | OH |
| Br | CH$_3$ | OCH$_2$CH$_3$ |
| Br | Cl | Cl |
| Br | Cl | OH |
| Br | Cl | OCH$_2$CH$_3$ |
| Br | Br | Cl |
| Br | Br | OH |
| Br | Br | OCH$_2$CH$_3$ |
| Cl | H | Cl |
| Cl | H | OH |
| Cl | H | OCH$_2$CH$_3$ |
| Cl | CH$_3$ | Cl |
| Cl | CH$_3$ | OH |
| Cl | CH$_3$ | OCH$_2$CH$_3$ |
| Cl | Cl | Cl |
| Cl | Cl | OH |
| Cl | Cl | OCH$_2$CH$_3$ |
| Cl | Br | Cl |
| Cl | Br | OH |
| Cl | Br | OCH$_2$CH$_3$ |
| CF$_3$ | H | Cl |
| CF$_3$ | H | OH |
| CF$_3$ | H | OCH$_2$CH$_3$ |
| CF$_3$ | CH$_3$ | Cl |
| CF$_3$ | CH$_3$ | OH |
| CF$_3$ | CH$_3$ | OCH$_2$CH$_3$ |
| CF$_3$ | Cl | Cl |
| CF$_3$ | Cl | OH |
| CF$_3$ | Cl | OCH$_2$CH$_3$ |
| CF$_3$ | Br | Cl |
| CF$_3$ | Br | OH |
| CF$_3$ | Br | OCH$_2$CH$_3$ |

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. $^1$H NMR spectra are reported in ppm downfield from tetramethylsilane; "s" means singlet, "d" means doublet, "dd" means doublet of doublets, "br s" means broad singlet. Room temperature is between about 20 and 25° C. Compound numbers refer to compounds in Index Table A.

Synthesis Example 1

Preparation of 6-bromo-N-[[2-chloro-5-(trifluoromethyl)phenyl]sulfonyl]imidazo[1,2-a]pyrimidine-2-carboxamide (compound 4)

To a solution of 2-amino-5-bromopyrimidine (3.79 g, 21.8 mmol) in 1,2-dimethoxyethane (200 mL) was added dropwise bromopyruvic acid (3.63 g, 21.8 mmol). The reaction mixture was stirred for 30 minutes, and then heated to reflux and stirred for 18 hours. The reaction mixture was then cooled to room temperature and concentrated under reduced pressure to obtain a solid. This solid was suspended in diethyl ether, and the suspension was filtered to isolate 6-bromoimidazo[1,2-a]pyrimidine-2-carboxylic acid hydrobromide and 6-bromoimidazo[1,2-a]pyrimidine-3-carboxylic acid hydrobromide as a 1:1 mixture. To this mixture of carboxylic acids (1.30 g, 5.37 mmol) was added a solution of 4-(dimethylamino)pyridine (1.966 g, 16.12 mmol) and 1-(3-dimethylaminopropyl)-3-ethylcarbodiimide hydrochloride (3.095 g, 16.12 mmol) in t-butanol (5 mL) and dichloromethane (15 mL). The reaction mixture was stirred for 5 minutes, 2-chloro-5-trifluoromethylbenzezenesulfonamide (1.394 g, 5.374 mmol) was added, and the reaction mixture was stirred at room temperature overnight. Dichloromethane (200 mL) was then added, the mixture was extracted with 1 N hydrochloric acid (1×100 mL), and the separated organic phase was dried over magnesium sulfate and concentrated under reduced pressure to afford a crude solid. The crude solid was purified by chromatography on silica gel eluting with a methanol/dichloromethane gradient to afford as the first eluting isomer 59.9 mg of the title compound, a compound of this invention, as a white solid, m.p.>250° C. $^1$H NMR (CDCl$_3$) δ 10.10 (br s, 1H), 8.46 (s, 1H), 8.27 (s, 1H), 7.86 (d, 1H), 7.54 (s, 1H), 7.38 (d, 1H), 7.09 (dd, 1H), 3.91 (s, 3H).

Synthesis Example 2

Preparation of N-[[2-chloro-5-(trifluoromethyl)phenyl]sulfonyl]-6-(trifluoromethyl)imidazo[1,2-a]pyrimidine-2-carboxamide (compound 6)

Step A: Preparation of 2-amino-5-(trifluoromethyl)pyrimidine

A 2-L flask fitted with a dry ice condenser and addition funnel was charged with dimethylsulfoxide (500 mL) and a 0.5 M solution of sulfuric acid in dimethylsulfoxide (400 mL), followed by the addition of 2-aminopyrimidine (20.0 g, 211 mmol). The reaction mixture was stirred vigorously for 5 minutes, and then a 1 M solution of iron(II) sulfate in water (60 mL) was added. Trifluoromethyl iodide (200 g, 1.02 moles) was added below the surface of the reaction mixture at room temperature. The reaction mixture was then cooled to 0° C., and 50% aqueous hydrogen peroxide (20 mL, 294 mmol) was added dropwise over one hour. The ice bath was then removed, and the reaction mixture was allowed to warm to room temperature over three hours. The reaction mixture was then carefully neutralized to pH 6.5 with aqueous sodium carbonate. The reaction mixture was then extracted with ethyl acetate (3×300 mL), and the combined organic extracts were dried over magnesium sulfate and concentrated under reduced pressure. The resulting oil was purified by chromatography on silica gel eluting with a hexane/ethyl acetate gradient to afford 4.51 g of the title compound as an off white solid. $^1$H NMR (CDCl$_3$) δ 8.51 (s, 2H), 5.55 (br s, 2H).

Step B: Preparation of the HBr salt of 6-(trifluoromethyl)imidazo[1,2-a]pyrimidine-2-carboxylic acid The product of Step A (1.0 g, 6.1 mmol) was added to a solution of bromopyruvic acid (1.025 g, 6.134 mmol) in dioxane (30 mL), and the reaction mixture was heated at reflux for 24 hours. The dioxane was removed under reduced pressure to give 798 mg of the title compound. $^1$H NMR ((CD$_3$)$_2$SO) δ 9.67 (s, 1H), 8.99 (s, 1H), 8.49 (s, 1H), 5.98 (br s, 2H).

Step C: Preparation of N-[[2-chloro-5-(trifluoromethyl)phenyl]sulfonyl]-6-(trifluoromethyl)imidazo[1,2-a]pyrimidine-2-carboxamide To the product of Step B (230 mg, 0.737 mmol) was added a solution of 4-(dimethylamino)pyridine (180 mg, 1.47 mmol) and 1-(3-dimethylaminopropyl)-3-ethylcarbodiimide hydrochloride (424 mg, 2.21 mmol) in t-butanol (5 mL) and dichloromethane (15 mL). The reaction mixture was stirred for 5 minutes, 2-chloro-5-(trifluoromethyl)benzenesulfonamide (191 mg, 0.737 mmol) was added, and the reaction mixture was stirred at room temperature overnight. Dichloromethane (200 mL) was then added, the mixture was extracted with 1 N hydrochloric acid (1×100 mL), and the separated organic phase was dried over magnesium sulfate and concentrated under reduced pressure to afford a crude solid. The crude solid was purified by chromatography on silica gel eluting with a methanol/dichloromethane gradient to afford 27.7 mg of the title compound, a compound of this invention, as a white solid, m.p. 211-212° C. $^1$H NMR (CD$_3$OD) δ 9.50 (s, 1H), 8.79 (s, 1H), 8.37-8.41 (m, 2H), 7.73 (d, 1H), 7.63 (d, 1H).

Synthesis Example 3

Preparation of N-[(2-chloro-5-methoxyphenyl)sulfonyl]-6-(trifluoromethyl)imidazo[1,2-a]pyrazine-2-carboxamide (compound 1)

Step A: Preparation of 6-(trifluoromethyl)imidazo[1,2-a]pyrazine-2-carboxylic acid ethyl ester To a solution of 2-amino-5-(trifluoromethyl)pyrazine (500 mg, 3.07 mmol) in 1,2-dimethoxyethane (10 mL) was added dropwise ethyl bromopyruvate (0.5 mL, 4.0 mmol). The reaction mixture was warmed to 60° C. for 72 hours. The reaction mixture was then cooled to room temperature, and water was added (10 mL) to precipitate a solid. The suspension was stirred for 10 minutes, filtered, and the isolated solid was washed with water to afford the desired ester which was used in the next step without further drying. $^1$H NMR (CDCl$_3$) δ 9.22 (s, 1H), 8.59 (s, 1H), 8.39 (s, 1H), 4.50 (q, 2H), 1.47 (t, 3H).

Step B: Preparation of 6-(trifluoromethyl)imidazo[1,2-a]pyrazine-2-carboxylic acid The product of Step A was dissolved in tetrahydrofuran (10 mL) and a solution of lithium hydroxide monohydrate (97 mg, 8.3 mmol) in water (5 mL) was added. The reaction mixture was stirred at room temperature for one hour, after which time the tetrahydrofuran was removed on a rotary evaporator under reduced pressure, and water was added (5 mL), followed by the addition of 1 N HCl (5 mL). The resulting suspension was filtered through a glass-fritted filter funnel, and the isolated solid was washed with water and dried over nitrogen to afford 451 mg of the title compound as a solid. $^1$H NMR ((CD$_3$)$_2$SO) δ 9.33 (s, 1H), 9.30 (s, 1H), 8.69 (s, 1H).

Step C: Preparation of N-[(2-chloro-5-methoxyphenyl)sulfonyl]-6-(trifluoromethyl)imidazo[1,2-a]pyrazine-2-carboxamide To the product of Step B (120 mg, 0.52 mmol) was added a solution of 4-(dimethylamino)pyridine (183 mg, 1.5 mmol) and 1-(3-dimethylaminopropyl)-3-ethylcarbodiimide hydrochloride (248 mg, 1.3 mmol) in t-butanol (5 mL) and dichloromethane (5 mL). The reaction mixture was stirred for 15 minutes, 2-chloro-5-methoxybenzenesulfonamide (92 mg, 0.41 mmol) was added, and stirring was continued at room temperature overnight. Dichloromethane (100 mL) was then added, the mixture was washed with 1 N hydrochloric acid (3×100 mL), and the combined organic phases were dried over magnesium sulfate and concentrated under reduced pressure to afford a solid. The solid was rinsed with diethyl ether and dried to afford. 89 mg of the title compound, a compound of this invention, as a white solid, m.p. 236-237° C. $^1$H NMR (CDCl$_3$) δ 9.99 (br s, 1H), 9.23 (s, 1H), 8.56 (s, 1H), 8.32 (s, 1H), 7.86 (s, 1H), 7.37 (d, 1H), 7.10 (dd, 1H) 3.91 (s, 3H).

By the procedures described herein together with methods known in the art, the following compounds of Tables 1 to 22 can be prepared. The following abbreviations are used in the Tables which follow: Me means methyl, Et means ethyl, OMe means methoxy, SMe means methylthio, and NMe$_2$ means dimethylamino.

TABLE 1

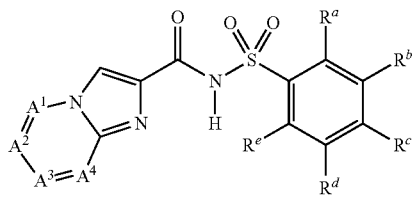

$A^1$ is N, $A^2$ is CCF$_3$, $A^3$ and $A^4$ are CH

| $R^a$ | $R^b$ | $R^c$ | $R^d$ | $R^e$ |
|---|---|---|---|---|
| H | H | H | H | H |
| H | Me | H | H | H |
| H | Et | H | H | H |
| H | F | H | H | H |
| H | Cl | H | H | H |
| H | Br | H | H | H |
| H | CF$_3$ | H | H | H |
| H | cyano | H | H | H |
| H | OMe | H | H | H |
| H | SMe | H | H | H |
| F | H | H | H | H |
| F | Me | H | H | H |
| F | Et | H | H | H |
| F | F | H | H | H |
| F | Cl | H | H | H |
| F | Br | H | H | H |
| F | CF$_3$ | H | H | H |
| F | cyano | H | H | H |
| F | OMe | H | H | H |
| F | SMe | H | H | H |
| Br | H | H | H | H |
| Br | Me | H | H | H |
| Br | Et | H | H | H |
| Br | F | H | H | H |
| Br | Cl | H | H | H |
| Br | Br | H | H | H |
| Br | CF$_3$ | H | H | H |
| Br | cyano | H | H | H |
| Br | OMe | H | H | H |
| Br | SMe | H | H | H |
| cyano | H | H | H | H |
| cyano | Me | H | H | H |
| cyano | Et | H | H | H |
| cyano | F | H | H | H |
| cyano | Cl | H | H | H |
| H | H | H | H | H |
| H | H | Me | H | H |
| H | H | Et | H | H |
| H | H | F | H | H |
| H | H | Cl | H | H |
| H | H | Br | H | H |
| H | H | CF$_3$ | H | H |
| H | H | cyano | H | H |
| H | H | OMe | H | H |
| H | H | SMe | H | H |
| F | H | H | H | H |
| F | H | Me | H | H |
| F | H | Et | H | H |
| F | H | F | H | H |
| F | H | Cl | H | H |
| F | H | Br | H | H |
| F | H | CF$_3$ | H | H |
| F | H | cyano | H | H |
| F | H | OMe | H | H |
| F | H | SMe | H | H |
| Br | H | H | H | H |
| Br | H | Me | H | H |
| Br | H | Et | H | H |
| Br | H | F | H | H |
| Br | H | Cl | H | H |
| Br | H | Br | H | H |
| Br | H | CF$_3$ | H | H |
| Br | H | cyano | H | H |
| Br | H | OMe | H | H |
| Br | H | SMe | H | H |
| cyano | H | H | H | H |
| cyano | H | Me | H | H |
| cyano | H | Et | H | H |
| cyano | H | F | H | H |

TABLE 1-continued

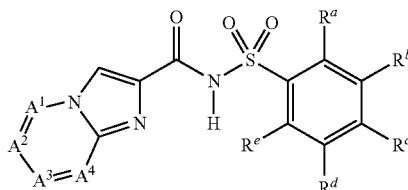

$A^1$ is N, $A^2$ is $CCF_3$, $A^3$ and $A^4$ are CH

| $R^a$ | $R^b$ | $R^c$ | $R^d$ | $R^e$ |
|---|---|---|---|---|
| cyano | H | Cl | H | H |
| H | H | H | H | H |
| H | H | H | Me | H |
| H | H | H | Et | H |
| H | H | H | F | H |
| H | H | H | Cl | H |
| H | H | H | Br | H |
| H | H | H | $CF_3$ | H |
| H | H | H | cyano | H |
| H | H | H | OMe | H |
| H | H | H | SMe | H |
| H | H | H | $CO_2Me$ | H |
| H | H | H | C(O)Me | H |
| H | H | H | $NMe_2$ | H |
| H | H | H | nitro | H |
| F | H | H | H | H |
| F | H | H | Me | H |
| F | H | H | Et | H |
| F | H | H | F | H |
| F | H | H | Cl | H |
| F | H | H | Br | H |
| F | H | H | $CF_3$ | H |
| F | H | H | cyano | H |
| F | H | H | OMe | H |
| F | H | H | SMe | H |
| F | H | H | $CO_2Me$ | H |
| F | H | H | C(O)Me | H |
| F | H | H | $NMe_2$ | H |
| F | H | H | nitro | H |
| Br | H | H | H | H |
| Br | H | H | Me | H |
| Br | H | H | Et | H |
| Br | H | H | F | H |
| Br | H | H | Cl | H |
| Br | H | H | Br | H |
| Br | H | H | $CF_3$ | H |
| Br | H | H | cyano | H |
| Br | H | H | OMe | H |
| Br | H | H | SMe | H |
| Br | H | H | $CO_2Me$ | H |
| Br | H | H | C(O)Me | H |
| Br | H | H | $NMe_2$ | H |
| Br | H | H | nitro | H |
| cyano | H | H | H | H |
| cyano | H | H | Me | H |
| cyano | H | H | Et | H |
| cyano | H | H | F | H |
| cyano | H | H | Cl | H |
| cyano | H | H | Br | H |
| cyano | H | H | $CF_3$ | H |
| H | H | Me | H | H |
| H | H | Me | Me | H |
| H | H | Me | Et | H |
| H | H | Me | F | H |
| H | H | Me | Cl | H |
| H | H | Me | Br | H |
| H | H | Me | $CF_3$ | H |
| H | H | Me | cyano | H |
| H | H | Me | OMe | H |
| H | H | Me | SMe | H |
| H | H | Me | $CO_2Me$ | H |
| H | H | Me | C(O)Me | H |
| H | H | Me | $NMe_2$ | H |
| H | H | Me | nitro | H |
| F | H | Me | H | H |
| F | H | Me | Me | H |

TABLE 1-continued

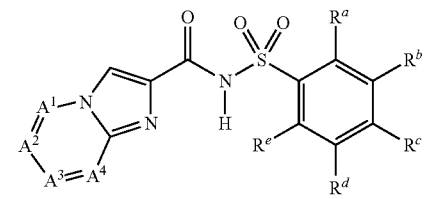

$A^1$ is N, $A^2$ is $CCF_3$, $A^3$ and $A^4$ are CH

| $R^a$ | $R^b$ | $R^c$ | $R^d$ | $R^e$ |
|---|---|---|---|---|
| F | H | Me | Et | H |
| F | H | Me | F | H |
| F | H | Me | Cl | H |
| F | H | Me | Br | H |
| F | H | Me | $CF_3$ | H |
| F | H | Me | cyano | H |
| F | H | Me | OMe | H |
| F | H | Me | SMe | H |
| F | H | Me | $CO_2Me$ | H |
| F | H | Me | C(O)Me | H |
| F | H | Me | $NMe_2$ | H |
| F | H | Me | nitro | H |
| Br | H | Me | H | H |
| Br | H | Me | Me | H |
| Br | H | Me | Et | H |
| Br | H | Me | F | H |
| Br | H | Me | Cl | H |
| Br | H | Me | Br | H |
| Br | H | Me | $CF_3$ | H |
| Br | H | Me | cyano | H |
| Br | H | Me | OMe | H |
| Br | H | Me | SMe | H |
| Br | H | Me | $CO_2Me$ | H |
| Br | H | Me | C(O)Me | H |
| Br | H | Me | $NMe_2$ | H |
| Br | H | Me | nitro | H |
| cyano | H | Me | H | H |
| cyano | H | Me | Me | H |
| cyano | H | Me | Et | H |
| cyano | H | Me | F | H |
| cyano | H | Me | Cl | H |
| cyano | H | Me | Br | H |
| cyano | H | Me | $CF_3$ | H |
| H | H | Cl | H | H |
| H | H | Cl | Me | H |
| H | H | Cl | Et | H |
| H | H | Cl | F | H |
| H | H | Cl | Cl | H |
| H | H | Cl | Br | H |
| H | H | Cl | $CF_3$ | H |
| H | H | Cl | cyano | H |
| H | H | Cl | OMe | H |
| H | H | Cl | SMe | H |
| H | H | Cl | $CO_2Me$ | H |
| H | H | Cl | C(O)Me | H |
| H | H | Cl | $NMe_2$ | H |
| H | H | Cl | nitro | H |
| F | H | Cl | H | H |
| F | H | Cl | Me | H |
| F | H | Cl | Et | H |
| F | H | Cl | F | H |
| F | H | Cl | Cl | H |
| F | H | Cl | Br | H |
| F | H | Cl | $CF_3$ | H |
| F | H | Cl | cyano | H |
| F | H | Cl | OMe | H |
| F | H | Cl | SMe | H |
| F | H | Cl | $CO_2Me$ | H |
| F | H | Cl | C(O)Me | H |
| F | H | Cl | $NMe_2$ | H |
| F | H | Cl | nitro | H |
| Br | H | Cl | H | H |
| Br | H | Cl | Me | H |
| Br | H | Cl | Et | H |
| Br | H | Cl | F | H |
| Br | H | Cl | Cl | H |

TABLE 1-continued

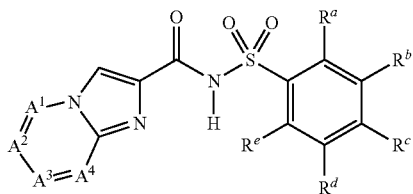

$A^1$ is N, $A^2$ is $CCF_3$, $A^3$ and $A^4$ are CH

| $R^a$ | $R^b$ | $R^c$ | $R^d$ | $R^e$ |
|---|---|---|---|---|
| Br | H | Cl | Br | H |
| Br | H | Cl | $CF_3$ | H |
| Br | H | Cl | cyano | H |
| Br | H | Cl | OMe | H |
| Br | H | Cl | SMe | H |
| Br | H | Cl | $CO_2Me$ | H |
| Br | H | Cl | C(O)Me | H |
| Br | H | Cl | $NMe_2$ | H |
| Br | H | Cl | nitro | H |
| cyano | H | Cl | H | H |
| cyano | H | Cl | Me | H |
| cyano | H | Cl | Et | H |
| cyano | H | Cl | F | H |
| cyano | H | Cl | Cl | H |
| cyano | H | Cl | Br | H |
| cyano | H | Cl | $CF_3$ | H |
| H | H | cyano | H | H |
| H | H | cyano | Me | H |
| H | H | cyano | Et | H |
| H | H | cyano | F | H |
| H | H | cyano | Cl | H |
| H | H | cyano | Br | H |
| H | H | cyano | $CF_3$ | H |
| H | H | cyano | cyano | H |
| H | H | cyano | OMe | H |
| H | H | cyano | SMe | H |
| H | H | cyano | $CO_2Me$ | H |
| H | H | cyano | C(O)Me | H |
| H | H | cyano | $NMe_2$ | H |
| H | H | cyano | nitro | H |
| F | H | cyano | H | H |
| F | H | cyano | Me | H |
| F | H | cyano | Et | H |
| F | H | cyano | F | H |
| F | H | cyano | Cl | H |
| F | H | cyano | Br | H |
| F | H | cyano | $CF_3$ | H |
| F | H | cyano | cyano | H |
| F | H | cyano | OMe | H |
| F | H | cyano | SMe | H |
| F | H | cyano | $CO_2Me$ | H |
| F | H | cyano | C(O)Me | H |
| F | H | cyano | $NMe_2$ | H |
| F | H | cyano | nitro | H |
| Br | H | cyano | H | H |
| Br | H | cyano | Me | H |
| Br | H | cyano | Et | H |
| Br | H | cyano | F | H |
| Br | H | cyano | Cl | H |
| Br | H | cyano | Br | H |
| Br | H | cyano | $CF_3$ | H |
| Br | H | cyano | cyano | H |
| Br | H | cyano | OMe | H |
| Br | H | cyano | SMe | H |
| Br | H | cyano | $CO_2Me$ | H |
| Br | H | cyano | C(O)Me | H |
| Br | H | cyano | $NMe_2$ | H |
| Br | H | cyano | nitro | H |
| cyano | H | cyano | H | H |
| cyano | H | cyano | Me | H |
| cyano | H | cyano | Et | H |
| cyano | H | cyano | F | H |
| cyano | H | cyano | Cl | H |
| cyano | H | cyano | Br | H |
| cyano | H | cyano | $CF_3$ | H |
| H | H | H | H | H |

TABLE 1-continued

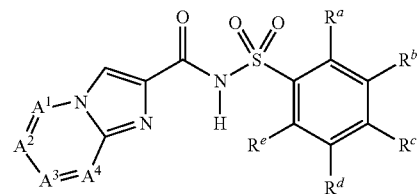

$A^1$ is N, $A^2$ is $CCF_3$, $A^3$ and $A^4$ are CH

| $R^a$ | $R^b$ | $R^c$ | $R^d$ | $R^e$ |
|---|---|---|---|---|
| H | H | H | H | Me |
| H | H | H | H | F |
| H | H | H | H | Cl |
| H | H | H | H | Br |
| F | H | H | H | H |
| F | H | H | H | Me |
| F | H | H | H | F |
| F | H | H | H | Cl |
| F | H | H | H | Br |
| Br | H | H | H | H |
| Br | H | H | H | Me |
| Br | H | H | H | F |
| Br | H | H | H | Cl |
| Br | H | H | H | Br |
| cyano | H | H | H | H |
| cyano | H | H | H | Me |
| Cl | H | H | $OCF_3$ | H |
| $OCF_3$ | H | H | Cl | H |
| Me | H | H | H | H |
| Me | Me | H | H | H |
| Me | Et | H | H | H |
| Me | F | H | H | H |
| Me | Cl | H | H | H |
| Me | Br | H | H | H |
| Me | $CF_3$ | H | H | H |
| Me | cyano | H | H | H |
| Me | OMe | H | H | H |
| Me | SMe | H | H | H |
| Cl | H | H | H | H |
| Cl | Me | H | H | H |
| Cl | Et | H | H | H |
| Cl | F | H | H | H |
| Cl | Cl | H | H | H |
| Cl | Br | H | H | H |
| Cl | $CF_3$ | H | H | H |
| Cl | cyano | H | H | H |
| Cl | OMe | H | H | H |
| Cl | SMe | H | H | H |
| $CF_3$ | H | H | H | H |
| $CF_3$ | Me | H | H | H |
| $CF_3$ | Et | H | H | H |
| $CF_3$ | F | H | H | H |
| $CF_3$ | Cl | H | H | H |
| $CF_3$ | Br | H | H | H |
| $CF_3$ | $CF_3$ | H | H | H |
| $CF_3$ | cyano | H | H | H |
| $CF_3$ | OMe | H | H | H |
| $CF_3$ | SMe | H | H | H |
| cyano | Br | H | H | H |
| cyano | $CF_3$ | H | H | H |
| cyano | cyano | H | H | H |
| cyano | OMe | H | H | H |
| cyano | SMe | H | H | H |
| Me | H | H | H | H |
| Me | H | Me | H | H |
| Me | H | Et | H | H |
| Me | H | F | H | H |
| Me | H | Cl | H | H |
| Me | H | Br | H | H |
| Me | H | $CF_3$ | H | H |
| Me | H | cyano | H | H |
| Me | H | OMe | H | H |
| Me | H | SMe | H | H |
| Cl | H | H | H | H |
| Cl | H | Me | H | H |
| Cl | H | Et | H | H |

TABLE 1-continued

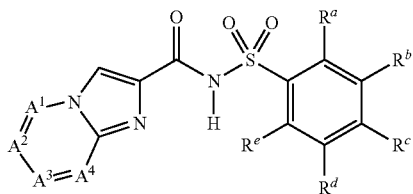

$A^1$ is N, $A^2$ is CCF$_3$, $A^3$ and $A^4$ are CH

| $R^a$ | $R^b$ | $R^c$ | $R^d$ | $R^e$ |
|---|---|---|---|---|
| Cl | H | F | H | H |
| Cl | H | Cl | H | H |
| Cl | H | Br | H | H |
| Cl | H | CF$_3$ | H | H |
| Cl | H | cyano | H | H |
| Cl | H | OMe | H | H |
| Cl | H | SMe | H | H |
| CF$_3$ | H | H | H | H |
| CF$_3$ | H | Me | H | H |
| CF$_3$ | H | Et | H | H |
| CF$_3$ | H | F | H | H |
| CF$_3$ | H | Cl | H | H |
| CF$_3$ | H | Br | H | H |
| CF$_3$ | H | CF$_3$ | H | H |
| CF$_3$ | H | cyano | H | H |
| CF$_3$ | H | OMe | H | H |
| CF$_3$ | H | SMe | H | H |
| cyano | H | Br | H | H |
| cyano | H | CF$_3$ | H | H |
| cyano | H | cyano | H | H |
| cyano | H | OMe | H | H |
| cyano | H | SMe | H | H |
| Me | H | H | H | H |
| Me | H | H | Me | H |
| Me | H | H | Et | H |
| Me | H | H | F | H |
| Me | H | H | Cl | H |
| Me | H | H | Br | H |
| Me | H | H | CF$_3$ | H |
| Me | H | H | cyano | H |
| Me | H | H | OMe | H |
| Me | H | H | SMe | H |
| Me | H | H | CO$_2$Me | H |
| Me | H | H | C(O)Me | H |
| Me | H | H | NMe$_2$ | H |
| Me | H | H | nitro | H |
| Cl | H | H | H | H |
| Cl | H | H | Me | H |
| Cl | H | H | Et | H |
| Cl | H | H | F | H |
| Cl | H | H | Cl | H |
| Cl | H | H | Br | H |
| Cl | H | H | CF$_3$ | H |
| Cl | H | H | cyano | H |
| Cl | H | H | OMe | H |
| Cl | H | H | SMe | H |
| Cl | H | H | CO$_2$Me | H |
| Cl | H | H | C(O)Me | H |
| Cl | H | H | NMe$_2$ | H |
| Cl | H | H | nitro | H |
| CF$_3$ | H | H | H | H |
| CF$_3$ | H | H | Me | H |
| CF$_3$ | H | H | Et | H |
| CF$_3$ | H | H | F | H |
| CF$_3$ | H | H | Cl | H |
| CF$_3$ | H | H | Br | H |
| CF$_3$ | H | H | CF$_3$ | H |
| CF$_3$ | H | H | cyano | H |
| CF$_3$ | H | H | OMe | H |
| CF$_3$ | H | H | SMe | H |
| CF$_3$ | H | H | CO$_2$Me | H |
| CF$_3$ | H | H | C(O)Me | H |
| CF$_3$ | H | H | NMe$_2$ | H |
| CF$_3$ | H | H | nitro | H |
| cyano | H | H | cyano | H |
| cyano | H | H | OMe | H |

TABLE 1-continued

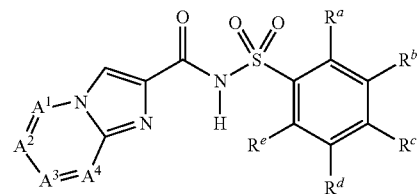

$A^1$ is N, $A^2$ is CCF$_3$, $A^3$ and $A^4$ are CH

| $R^a$ | $R^b$ | $R^c$ | $R^d$ | $R^e$ |
|---|---|---|---|---|
| cyano | H | H | SMe | H |
| cyano | H | H | CO$_2$Me | H |
| cyano | H | H | C(O)Me | H |
| cyano | H | H | NMe$_2$ | H |
| cyano | H | H | nitro | H |
| Me | H | Me | H | H |
| Me | H | Me | Me | H |
| Me | H | Me | Et | H |
| Me | H | Me | F | H |
| Me | H | Me | Cl | H |
| Me | H | Me | Br | H |
| Me | H | Me | CF$_3$ | H |
| Me | H | Me | cyano | H |
| Me | H | Me | OMe | H |
| Me | H | Me | SMe | H |
| Me | H | Me | CO$_2$Me | H |
| Me | H | Me | C(O)Me | H |
| Me | H | Me | NMe$_2$ | H |
| Me | H | Me | nitro | H |
| Cl | H | Me | H | H |
| Cl | H | Me | Me | H |
| Cl | H | Me | Et | H |
| Cl | H | Me | F | H |
| Cl | H | Me | Cl | H |
| Cl | H | Me | Br | H |
| Cl | H | Me | CF$_3$ | H |
| Cl | H | Me | cyano | H |
| Cl | H | Me | OMe | H |
| Cl | H | Me | SMe | H |
| Cl | H | Me | CO$_2$Me | H |
| Cl | H | Me | C(O)Me | H |
| Cl | H | Me | NMe$_2$ | H |
| Cl | H | Me | nitro | H |
| CF$_3$ | H | Me | H | H |
| CF$_3$ | H | Me | Me | H |
| CF$_3$ | H | Me | Et | H |
| CF$_3$ | H | Me | F | H |
| CF$_3$ | H | Me | Cl | H |
| CF$_3$ | H | Me | Br | H |
| CF$_3$ | H | Me | CF$_3$ | H |
| CF$_3$ | H | Me | cyano | H |
| CF$_3$ | H | Me | OMe | H |
| CF$_3$ | H | Me | SMe | H |
| CF$_3$ | H | Me | CO$_2$Me | H |
| CF$_3$ | H | Me | C(O)Me | H |
| CF$_3$ | H | Me | NMe$_2$ | H |
| CF$_3$ | H | Me | nitro | H |
| cyano | H | Me | cyano | H |
| cyano | H | Me | OMe | H |
| cyano | H | Me | SMe | H |
| cyano | H | Me | CO$_2$Me | H |
| cyano | H | Me | C(O)Me | H |
| cyano | H | Me | NMe$_2$ | H |
| cyano | H | Me | nitro | H |
| Me | H | Cl | H | H |
| Me | H | Cl | Me | H |
| Me | H | Cl | Et | H |
| Me | H | Cl | F | H |
| Me | H | Cl | Cl | H |
| Me | H | Cl | Br | H |
| Me | H | Cl | CF$_3$ | H |
| Me | H | Cl | cyano | H |
| Me | H | Cl | OMe | H |
| Me | H | Cl | SMe | H |
| Me | H | Cl | CO$_2$Me | H |
| Me | H | Cl | C(O)Me | H |

TABLE 1-continued

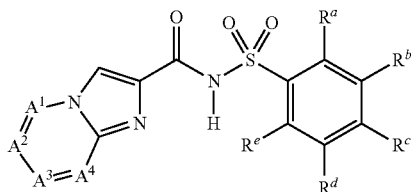

A¹ is N, A² is CCF₃, A³ and A⁴ are CH

| $R^a$ | $R^b$ | $R^c$ | $R^d$ | $R^e$ |
|---|---|---|---|---|
| Me | H | Cl | NMe₂ | H |
| Me | H | Cl | nitro | H |
| Cl | H | Cl | H | H |
| Cl | H | Cl | Me | H |
| Cl | H | Cl | Et | H |
| Cl | H | Cl | F | H |
| Cl | H | Cl | Cl | H |
| Cl | H | Cl | Br | H |
| Cl | H | Cl | CF₃ | H |
| Cl | H | Cl | cyano | H |
| Cl | H | Cl | OMe | H |
| Cl | H | Cl | SMe | H |
| Cl | H | Cl | CO₂Me | H |
| Cl | H | Cl | C(O)Me | H |
| Cl | H | Cl | NMe₂ | H |
| Cl | H | Cl | nitro | H |
| CF₃ | H | Cl | H | H |
| CF₃ | H | Cl | Me | H |
| CF₃ | H | Cl | Et | H |
| CF₃ | H | Cl | F | H |
| CF₃ | H | Cl | Cl | H |
| CF₃ | H | Cl | Br | H |
| CF₃ | H | Cl | CF₃ | H |
| CF₃ | H | Cl | cyano | H |
| CF₃ | H | Cl | OMe | H |
| CF₃ | H | Cl | SMe | H |
| CF₃ | H | Cl | CO₂Me | H |
| CF₃ | H | Cl | C(O)Me | H |
| CF₃ | H | Cl | NMe₂ | H |
| CF₃ | H | Cl | nitro | H |
| cyano | H | Cl | cyano | H |
| cyano | H | Cl | OMe | H |
| cyano | H | Cl | SMe | H |
| cyano | H | Cl | CO₂Me | H |
| cyano | H | Cl | C(O)Me | H |
| cyano | H | Cl | NMe₂ | H |
| cyano | H | Cl | nitro | H |
| Me | H | cyano | H | H |
| Me | H | cyano | Me | H |
| Me | H | cyano | Et | H |
| Me | H | cyano | F | H |
| Me | H | cyano | Cl | H |
| Me | H | cyano | Br | H |
| Me | H | cyano | CF₃ | H |
| Me | H | cyano | cyano | H |
| Me | H | cyano | OMe | H |
| Me | H | cyano | SMe | H |
| Me | H | cyano | CO₂Me | H |
| Me | H | cyano | C(O)Me | H |
| Me | H | cyano | NMe₂ | H |
| Me | H | cyano | nitro | H |
| Cl | H | cyano | H | H |
| Cl | H | cyano | Me | H |
| Cl | H | cyano | Et | H |
| Cl | H | cyano | F | H |
| Cl | H | cyano | Cl | H |
| Cl | H | cyano | Br | H |
| Cl | H | cyano | CF₃ | H |
| Cl | H | cyano | cyano | H |
| Cl | H | cyano | OMe | H |
| Cl | H | cyano | SMe | H |
| Cl | H | cyano | CO₂Me | H |
| Cl | H | cyano | C(O)Me | H |
| Cl | H | cyano | NMe₂ | H |
| Cl | H | cyano | nitro | H |
| CF₃ | H | cyano | H | H |

TABLE 1-continued

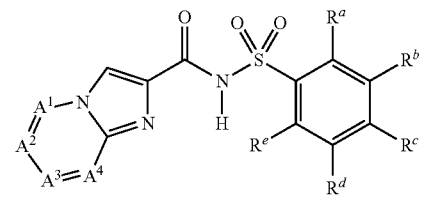

A¹ is N, A² is CCF₃, A³ and A⁴ are CH

| $R^a$ | $R^b$ | $R^c$ | $R^d$ | $R^e$ |
|---|---|---|---|---|
| CF₃ | H | cyano | Me | H |
| CF₃ | H | cyano | Et | H |
| CF₃ | H | cyano | F | H |
| CF₃ | H | cyano | Cl | H |
| CF₃ | H | cyano | Br | H |
| CF₃ | H | cyano | CF₃ | H |
| CF₃ | H | cyano | cyano | H |
| CF₃ | H | cyano | OMe | H |
| CF₃ | H | cyano | SMe | H |
| CF₃ | H | cyano | CO₂Me | H |
| CF₃ | H | cyano | C(O)Me | H |
| CF₃ | H | cyano | NMe₂ | H |
| CF₃ | H | cyano | nitro | H |
| cyano | H | cyano | cyano | H |
| cyano | H | cyano | OMe | H |
| cyano | H | cyano | SMe | H |
| cyano | H | cyano | CO₂Me | H |
| cyano | H | cyano | C(O)Me | H |
| cyano | H | cyano | NMe₂ | H |
| cyano | H | cyano | nitro | H |
| Me | H | H | H | H |
| Me | H | H | H | Me |
| Me | H | H | H | F |
| Me | H | H | H | Cl |
| Me | H | H | H | Br |
| Cl | H | H | H | H |
| Cl | H | H | H | Me |
| Cl | H | H | H | F |
| Cl | H | H | H | Cl |
| Cl | H | H | H | Br |
| CF₃ | H | H | H | H |
| CF₃ | H | H | H | Me |
| CF₃ | H | H | H | F |
| CF₃ | H | H | H | Cl |
| CF₃ | H | H | H | Br |
| cyano | H | H | H | F |
| cyano | H | H | H | Cl |
| cyano | H | H | H | Br |

Table 2

Table 2 is constructed the same as Table 1, except that A² is CBr. For example, the first compound in Table 2 wherein A¹ is N, A² is CBr, A³ and A⁴ are CH, and $R^a$ through $R^e$ are H is the structure shown immediately below.

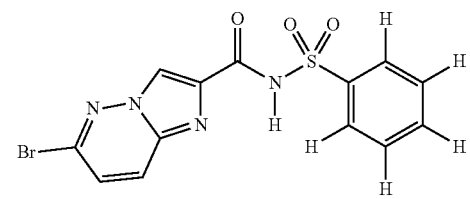 [SMILES: O=C(NS(=O)(=O)c1ccccc1)c1cn2nc(Br)ccc2n1]

Table 3

Table 3 is constructed the same as Table 1, except that A² is CCF₃ and A⁴ is CCl. For example, the first compound in Table 3 wherein $A^1$ is N, $A^2$ is $CCF_3$, $A^3$ is CH, $A^4$ is CCl, and $R^a$ through $R^e$ are H is the structure shown immediately below.

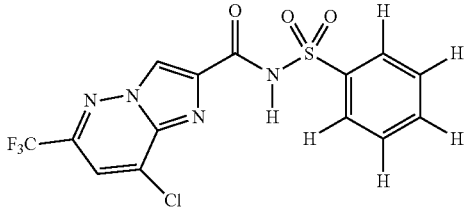 [SMILES: O=C(NS(=O)(=O)c1ccccc1)c1cn2nc(C(F)(F)F)cc(Cl)c2n1]

Table 4

Table 4 is constructed the same as Table 1, except that $A^2$ is CBr and $A^4$ is CCl. For example, the first compound in Table 4 wherein $A^1$ is N, $A^2$ is CBr, $A^3$ is CH, $A^4$ is CCl, and $R^a$ through $R^e$ are H is the structure shown immediately below.

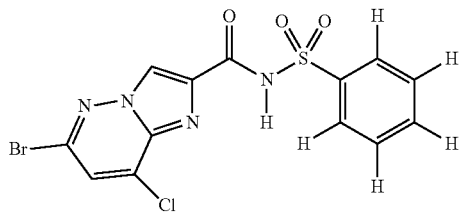 [SMILES: O=C(NS(=O)(=O)c1ccccc1)c1cn2nc(Br)cc(Cl)c2n1]

Table 5

Table 5 is constructed the same as Table 1, except that $A^1$ is CH and $A^2$ is N. For example, the first compound in Table 5 wherein $A^1$ is CH, $A^2$ is N, $A^3$ is CH, $A^4$ is CH, and $R^a$ through $R^e$ are H is the structure shown immediately below.

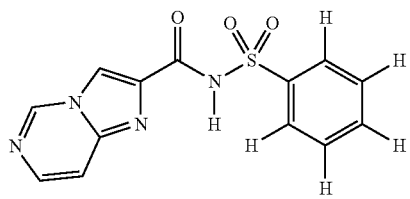 [SMILES: O=C(NS(=O)(=O)c1ccccc1)c1cn2cnccc2n1]

Table 6

Table 6 is constructed the same as Table 1, except that $A^1$ is CH, $A^2$ is N and $A^4$ is CCl. For example, the first compound in Table 6 wherein $A^1$ is CH, $A^2$ is N, $A^3$ is CH, $A^4$ is CCl, and $R^a$ through $R^e$ are H is the structure shown immediately below.

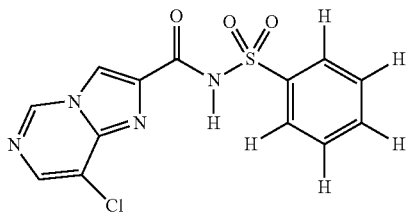 [SMILES: O=C(NS(=O)(=O)c1ccccc1)c1cn2cncc(Cl)c2n1]

Table 7

Table 7 is constructed the same as Table 1, except that $A^1$ is CH and $A^3$ is N. For example, the first compound in Table 7 wherein $A^1$ is CH, $A^2$ is $CCF_3$, $A^3$ is N, $A^4$ is CH, and $R^a$ through $R^e$ are H is the structure shown immediately below.

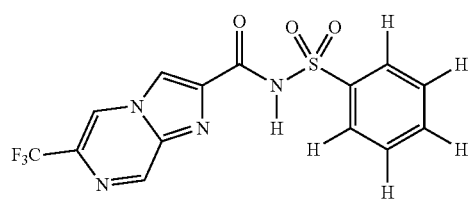 [SMILES: O=C(NS(=O)(=O)c1ccccc1)c1cn2cc(C(F)(F)F)ncc2n1]

Table 8

Table 8 is constructed the same as Table 1, except that $A^1$ is CH, $A^2$ is CBr, and $A^3$ is N. For example, the first compound in Table 8 wherein $A^1$ is CH, $A^2$ is CBr, $A^3$ is N, $A^4$ is CH, and $R^a$ through $R^e$ are is the structure shown immediately below.

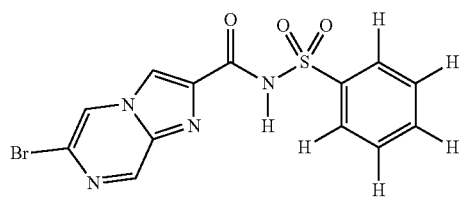 [SMILES: O=C(NS(=O)(=O)c1ccccc1)c1cn2cc(Br)ncc2n1]

Table 9

Table 9 is constructed the same as Table 1, except that $A^1$ is CH, $A^3$ is N, and A4 is CCl. For example, the first compound in Table 9 wherein $A^1$ is CH, $A^2$ is $CCF_3$, $A^3$ is N, $A^4$ is CCl, and $R^a$ through $R^e$ are H is the structure shown immediately below.

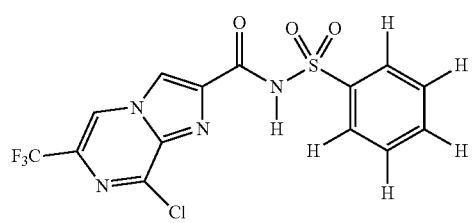 [SMILES: O=C(NS(=O)(=O)c1ccccc1)c1cn2cc(C(F)(F)F)nc(Cl)c2n1]

Table 10

Table 10 is constructed the same as Table 1, except that $A^1$ is CH, $A^2$ is CBr, $A^3$ is N, and $A^4$ is CCl. For example, the first compound in Table 10 wherein $A^1$ is CH, $A^2$ is CBr, $A^3$ is N, $A^4$ is CCl, and $R^a$ through $R^e$ are H is the structure shown immediately below.

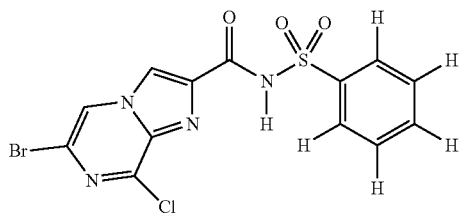 [SMILES: O=C(NS(=O)(=O)c1ccccc1)c1cn2cc(Br)nc(Cl)c2n1]

Table 11

Table 11 is constructed the same as Table 1, except that $A^1$ is CH and $A^4$ is N. For example, the first compound in Table 11 wherein $A^1$ is CH, $A^2$ is $CCF_3$, $A^3$ is CH, $A^4$ is N, and $R^a$ through $R^e$ are H is the structure shown immediately below.

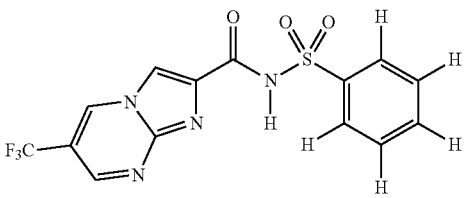 [SMILES: O=C(NS(=O)(=O)c1ccccc1)c1cn2cc(C(F)(F)F)cnc2n1]

Table 12

Table 12 is constructed the same as Table 1, except that $A^1$ is CH, $A^2$ is CBr, and $A^4$ is N. For example, the first compound in Table 12 wherein $A^1$ is CH, $A^2$ is CBr, $A^3$ is CH, $A^4$ is N, and $R^a$ through $R^e$ are H is the structure shown immediately below.

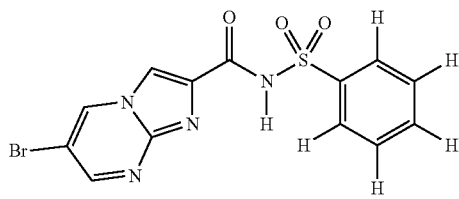 [SMILES: O=C(NS(=O)(=O)c1ccccc1)c1cn2cc(Br)cnc2n1]

TABLE 13

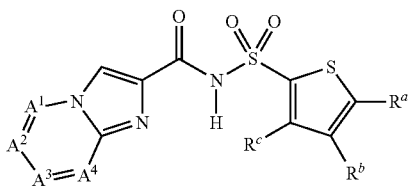

| $R^a$ | $R^b$ | $R^c$ |
|---|---|---|
| $A^1$ is CH, $A^2$ is $CCF_3$, $A^3$ is N, $A^4$ is CH | | |
| H | H | H |
| H | H | Me |
| H | H | Cl |
| H | H | Br |
| H | Me | H |
| H | Me | Me |
| H | Me | Cl |
| H | Me | Br |
| H | Et | H |
| H | Et | Me |
| H | Et | Cl |
| H | Et | Br |
| H | Cl | H |
| H | Cl | Me |
| H | Cl | Cl |
| H | Cl | Br |
| Br | H | H |
| Br | H | Me |
| Br | H | Cl |
| Br | H | Br |
| Br | Me | H |
| Br | Me | Me |
| Br | Me | Cl |
| Br | Me | Br |
| Br | Et | H |
| Br | Et | Me |
| Br | Et | Cl |
| Br | Et | Br |
| Br | Cl | H |
| Br | Cl | Me |
| Br | Cl | Cl |
| Br | Cl | Br |
| Me | H | H |
| Me | H | Me |
| Me | H | Cl |
| Me | H | Br |
| Me | Me | H |
| Me | Me | Me |
| Me | Me | Cl |
| Me | Me | Br |
| Me | Et | H |
| Me | Et | Me |
| Me | Et | Cl |
| Me | Et | Br |
| Me | Cl | H |
| Me | Cl | Me |
| Me | Cl | Cl |
| Me | Cl | Br |
| Et | H | H |
| Et | H | Me |
| Et | H | Cl |
| Et | H | Br |
| Et | Me | H |
| Et | Me | Me |
| Et | Me | Cl |
| Et | Me | Br |
| Et | Et | H |
| Et | Et | Me |
| Et | Et | Cl |
| Et | Et | Br |
| Et | Cl | H |
| Et | Cl | Me |
| Et | Cl | Cl |
| Et | Cl | Br |
| Cl | H | H |
| Cl | H | Me |

TABLE 13-continued

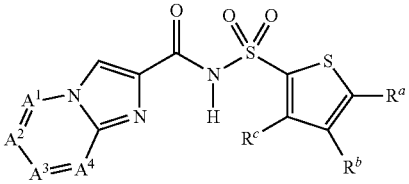

| $R^a$ | $R^b$ | $R^c$ |
|---|---|---|
| Cl | H | Cl |
| Cl | H | Br |
| Cl | Me | H |
| Cl | Me | Me |
| Cl | Me | Cl |
| Cl | Me | Br |
| Cl | Et | H |
| Cl | Et | Me |
| Cl | Et | Cl |
| Cl | Et | Br |
| Cl | Cl | H |
| Cl | Cl | Me |
| Cl | Cl | Cl |
| Cl | Cl | Br |
| $A^1$ is CH, $A^2$ is CBr, $A^3$ is N, $A^4$ is CH | | |
| H | H | H |
| H | H | Me |
| H | H | Cl |
| H | H | Br |
| H | Me | H |
| H | Me | Me |
| H | Me | Cl |
| H | Me | Br |
| H | Et | H |
| H | Et | Me |
| H | Et | Cl |
| H | Et | Br |
| H | Cl | H |
| H | Cl | Me |
| H | Cl | Cl |
| H | Cl | Br |
| Br | H | H |
| Br | H | Me |
| Br | H | Cl |
| Br | H | Br |
| Br | Me | H |
| Br | Me | Me |
| Br | Me | Cl |
| Br | Me | Br |
| Br | Et | H |
| Br | Et | Me |
| Br | Et | Cl |
| Br | Et | Br |
| Br | Cl | H |
| Br | Cl | Me |
| Br | Cl | Cl |
| Br | Cl | Br |
| Me | H | H |
| Me | H | Me |
| Me | H | Cl |
| Me | H | Br |
| Me | Me | H |
| Me | Me | Me |
| Me | Me | Cl |
| Me | Me | Br |
| Me | Et | H |
| Me | Et | Me |
| Me | Et | Cl |
| Me | Et | Br |
| Me | Cl | H |
| Me | Cl | Me |
| Me | Cl | Cl |
| Me | Cl | Br |
| Et | H | H |
| Et | H | Me |
| Et | H | Cl |
| Et | H | Br |

TABLE 13-continued

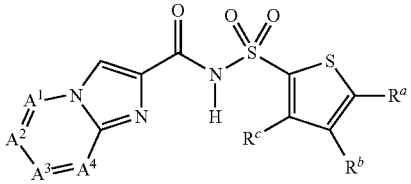

| $R^a$ | $R^b$ | $R^c$ |
|---|---|---|
| Et | Me | H |
| Et | Me | Me |
| Et | Me | Cl |
| Et | Me | Br |
| Et | Et | H |
| Et | Et | Me |
| Et | Et | Cl |
| Et | Et | Br |
| Et | Cl | H |
| Et | Cl | Me |
| Et | Cl | Cl |
| Et | Cl | Br |
| Cl | H | H |
| Cl | H | Me |
| Cl | H | Cl |
| Cl | H | Br |
| Cl | Me | H |
| Cl | Me | Me |
| Cl | Me | Cl |
| Cl | Me | Br |
| Cl | Et | H |
| Cl | Et | Me |
| Cl | Et | Cl |
| Cl | Et | Br |
| Cl | Cl | H |
| Cl | Cl | Me |
| Cl | Cl | Cl |
| Cl | Cl | Br |

TABLE 14

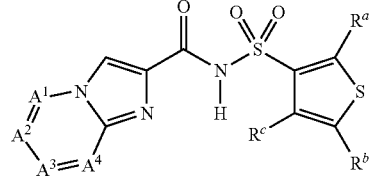

| $R^a$ | $R^b$ | $R^c$ |
|---|---|---|
| $A^1$ is CH, $A^2$ is CCF$_3$, $A^3$ is N, $A^4$ is CH | | |
| H | H | H |
| H | H | Me |
| H | H | Cl |
| H | Me | H |
| H | Me | Me |
| H | Me | Cl |
| H | Et | H |
| H | Et | Me |
| H | Et | Cl |
| Et | H | H |
| Et | H | Me |
| Et | H | Cl |
| Et | Me | H |
| Et | Me | Me |
| Et | Me | Cl |
| Et | Et | H |
| Et | Et | Me |
| Et | Et | Cl |
| Me | H | H |
| Me | H | Me |
| Me | H | Cl |

TABLE 14-continued

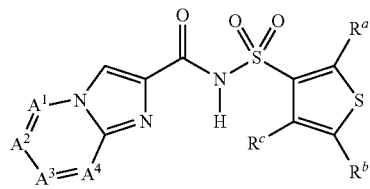

| Rª | Rᵇ | Rᶜ |
|---|---|---|
| Me | Me | H |
| Me | Me | Me |
| Me | Me | Cl |
| Me | Et | H |
| Me | Et | Me |
| Me | Et | Cl |
| Br | H | H |
| Br | H | Me |
| Br | H | Cl |
| Br | Me | H |
| Br | Me | Me |
| Br | Me | Cl |
| Br | Et | H |
| Br | Et | Me |
| Br | Et | Cl |
| Cl | H | H |
| Cl | H | Me |
| Cl | H | Cl |
| Cl | Me | H |
| Cl | Me | Me |
| Cl | Me | Cl |
| Cl | Et | H |
| Cl | Et | Me |
| Cl | Et | Cl |
| A¹ is CH, A² is CBr, A³ is N, A⁴ is CH | | |
| H | H | H |
| H | H | Me |
| H | H | Cl |
| H | Me | H |
| H | Me | Me |
| H | Me | Cl |
| H | Et | H |
| H | Et | Me |
| H | Et | Cl |
| Et | H | H |
| Et | H | Me |
| Et | H | Cl |
| Et | Me | H |
| Et | Me | Me |
| Et | Me | Cl |
| Et | Et | H |
| Et | Et | Me |
| Et | Et | Cl |
| Me | H | H |
| Me | H | Me |
| Me | H | Cl |
| Me | Me | H |
| Me | Me | Me |
| Me | Me | Cl |
| Me | Et | H |
| Me | Et | Me |
| Me | Et | Cl |
| Br | H | H |
| Br | H | Me |
| Br | H | Cl |
| Br | Me | H |
| Br | Me | Me |
| Br | Me | Cl |
| Br | Et | H |
| Br | Et | Me |
| Br | Et | Cl |
| Cl | H | H |
| Cl | H | Me |
| Cl | H | Cl |
| Cl | Me | H |
| Cl | Me | Me |
| Cl | Me | Cl |

TABLE 14-continued

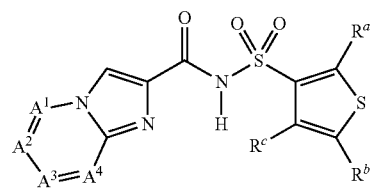

| Rª | Rᵇ | Rᶜ |
|---|---|---|
| Cl | Et | H |
| Cl | Et | Me |
| Cl | Et | Cl |

TABLE 15

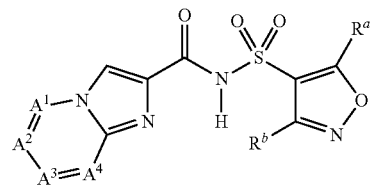

| Rª | Rᵇ |
|---|---|
| A¹ is CH, A² is CCF₃, A³ is N, A⁴ is CH | |
| H | H |
| H | Me |
| H | Cl |
| Me | H |
| Me | Me |
| Me | Cl |
| Cl | H |
| Cl | Me |
| Cl | Cl |
| A¹ is CH, A² is CBr, A³ is N, A⁴ is CH | |
| H | H |
| H | Me |
| H | Cl |
| Me | H |
| Me | Me |
| Me | Cl |
| Cl | H |
| Cl | Me |
| Cl | Cl |

TABLE 16

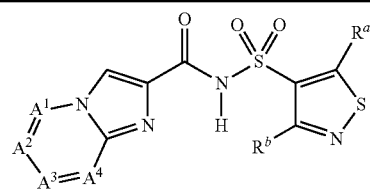

| Rª | Rᵇ |
|---|---|
| A¹ is CH, A² is CCF₃, A³ is N, A⁴ is CH | |
| H | H |
| H | Me |
| H | Cl |
| Me | H |
| Me | Me |
| Me | Cl |
| Cl | H |

TABLE 16-continued

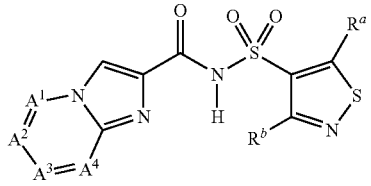

| $R^a$ | $R^b$ |
|---|---|
| Cl | Me |
| Cl | Cl |
| $A^1$ is CH, $A^2$ is CBr, $A^3$ is N, $A^4$ is CH | |
| H | H |
| H | Me |
| H | Cl |
| Me | H |
| Me | Me |
| Me | Cl |
| Cl | H |
| Cl | Me |
| Cl | Cl |

TABLE 17

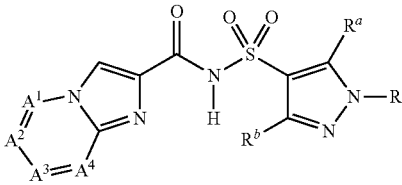

| $R^a$ | $R^b$ | $R^c$ |
|---|---|---|
| $A^1$ is CH, $A^2$ is CCF$_3$, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |

TABLE 17-continued

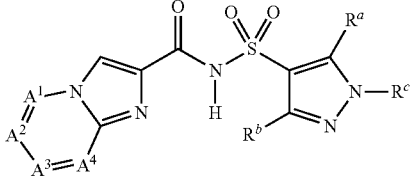

| $R^a$ | $R^b$ | $R^c$ |
|---|---|---|
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |
| $A^1$ is CH, $A^2$ is CBr, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Cl | Cl | Me |
| Cl | Cl | Et |

TABLE 17-continued

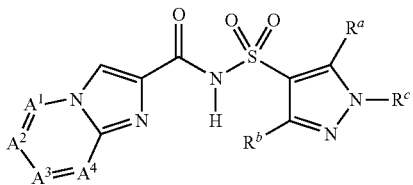

| $R^a$ | $R^b$ | $R^c$ |
|---|---|---|
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |

TABLE 17a

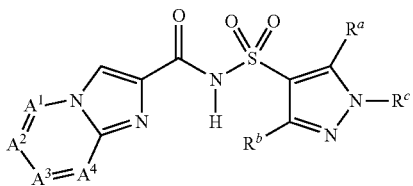

| $R^a$ | $R^b$ | $R^c$ |
|---|---|---|
| \multicolumn{3}{l}{$A^1$ is CH, $A^2$ is CCF$_3$, $A^3$ is N, $A^4$ is CH} |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |

TABLE 17a-continued

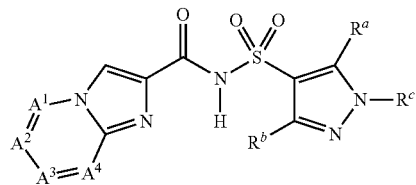

| $R^a$ | $R^b$ | $R^c$ |
|---|---|---|
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |
| \multicolumn{3}{l}{$A^1$ is CH, $A^2$ is CBr, $A^3$ is N, $A^4$ is CH} |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |

TABLE 17a-continued

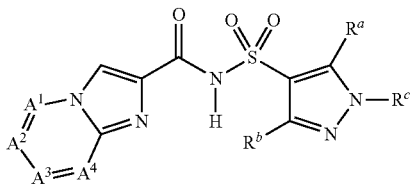

| $R^a$ | $R^b$ | $R^c$ |
|---|---|---|
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |

TABLE 17b

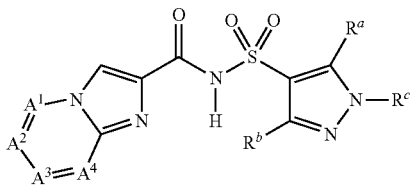

| $R^a$ | $R^b$ | $R^c$ |
|---|---|---|
| $A^1$ is CH, $A^2$ is CCF$_3$, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |

TABLE 17b-continued

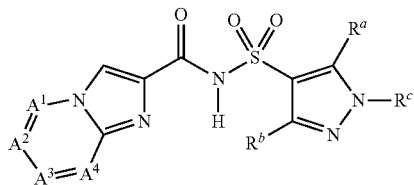

| $R^a$ | $R^b$ | $R^c$ |
|---|---|---|
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |
| $A^1$ is CH, $A^2$ is CBr, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |

TABLE 17b-continued

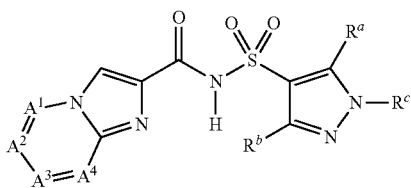

| $R^a$ | $R^b$ | $R^c$ |
|---|---|---|
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |

TABLE 18

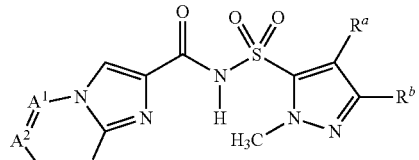

| $R^a$ | $R^b$ |
|---|---|
| $A^1$ is CH, $A^2$ is $CCF_3$, $A^3$ is N, $A^4$ is CH | |
| H | H |
| H | Cl |
| H | Me |
| H | Et |
| H | i-Pr |
| H | n-Pr |
| H | OMe |
| Me | H |
| Me | Cl |
| Me | Me |
| Me | Et |
| Me | i-Pr |
| Me | n-Pr |
| Me | OMe |
| Cl | H |
| Cl | Cl |
| Cl | Me |
| Cl | Et |
| Cl | i-Pr |
| Cl | n-Pr |
| Cl | OMe |
| Br | H |
| Br | Cl |
| Br | Me |
| Br | Et |
| Br | i-Pr |
| Br | n-Pr |
| Br | OMe |
| $A^1$ is CH, $A^2$ is CBr, $A^3$ is N, $A^4$ is CH | |
| H | H |
| H | Cl |
| H | Me |
| H | Et |
| H | i-Pr |
| H | n-Pr |
| H | OMe |
| Me | H |
| Me | Cl |
| Me | Me |
| Me | Et |
| Me | i-Pr |
| Me | n-Pr |
| Me | OMe |
| Cl | H |
| Cl | Cl |
| Cl | Me |
| Cl | Et |
| Cl | i-Pr |
| Cl | n-Pr |
| Cl | OMe |
| Br | H |
| Br | Cl |
| Br | Me |
| Br | Et |
| Br | i-Pr |
| Br | n-Pr |
| Br | OMe |

TABLE 19

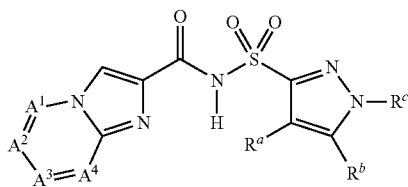

| $R^a$ | $R^b$ | $R^c$ |
|---|---|---|
| $A^1$ is CH, $A^2$ is CCF$_3$, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |

TABLE 19-continued

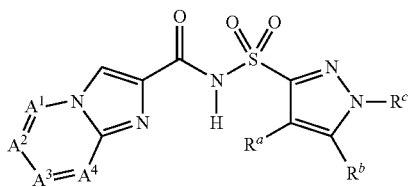

| $R^a$ | $R^b$ | $R^c$ |
|---|---|---|
| $A^1$ is CH, $A^2$ is CBr, $A^3$ is N, $A^4$ is CH | | |
| H | H | Me |
| H | H | Et |
| H | H | i-Pr |
| H | H | n-Pr |
| Br | H | Me |
| Br | H | Et |
| Br | H | i-Pr |
| Br | H | n-Pr |
| Cl | Me | Me |
| Cl | Me | Et |
| Cl | Me | i-Pr |
| Cl | Me | n-Pr |
| Me | Cl | Me |
| Me | Cl | Et |
| Me | Cl | i-Pr |
| Me | Cl | n-Pr |
| H | Br | Me |
| H | Br | Et |
| H | Br | i-Pr |
| H | Br | n-Pr |
| Br | Br | Me |
| Br | Br | Et |
| Br | Br | i-Pr |
| Br | Br | n-Pr |
| Me | H | Me |
| Me | H | Et |
| Me | H | i-Pr |
| Me | H | n-Pr |
| H | Me | Me |
| H | Me | Et |
| H | Me | i-Pr |
| H | Me | n-Pr |
| Br | Me | Me |
| Br | Me | Et |
| Br | Me | i-Pr |
| Br | Me | n-Pr |
| Cl | Cl | Me |
| Cl | Cl | Et |
| Cl | Cl | i-Pr |
| Cl | Cl | n-Pr |
| Me | Br | Me |
| Me | Br | Et |
| Me | Br | i-Pr |
| Me | Br | n-Pr |
| Cl | H | Me |
| Cl | H | Et |
| Cl | H | i-Pr |
| Cl | H | n-Pr |
| Me | Me | Me |
| Me | Me | Et |
| Me | Me | i-Pr |
| Me | Me | n-Pr |
| H | Cl | Me |
| H | Cl | Et |
| H | Cl | i-Pr |
| H | Cl | n-Pr |
| Br | Cl | Me |
| Br | Cl | Et |
| Br | Cl | i-Pr |
| Br | Cl | n-Pr |
| Cl | Br | Me |
| Cl | Br | Et |
| Cl | Br | i-Pr |
| Cl | Br | n-Pr |

TABLE 20

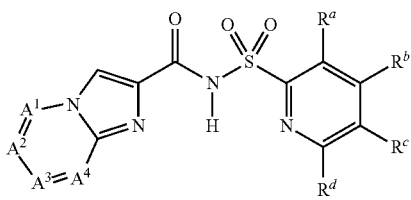

| $R^a$ | $R^b$ | $R^c$ | $R^d$ | $R^a$ | $R^b$ | $R^c$ | $R^d$ |
|---|---|---|---|---|---|---|---|
| \multicolumn{8}{c}{$A^1$ is CH, $A^2$ is CCF$_3$, $A^3$ is N, $A^4$ is CH} ||||||||
| Me | H | H | H | Cl | H | H | H |
| Me | H | H | Me | Cl | H | H | Me |
| Me | H | H | OMe | Cl | H | H | OMe |
| Me | OMe | H | H | Cl | OMe | H | H |
| Me | OMe | H | Me | Cl | OMe | H | Me |
| Me | OMe | H | OMe | Cl | OMe | H | OMe |
| Me | H | Me | H | Cl | H | Me | H |
| Me | H | Me | Me | Cl | H | Me | Me |
| Me | H | Me | OMe | Cl | H | Me | OMe |
| Me | OMe | Me | H | Cl | OMe | Me | H |
| Me | OMe | Me | Me | Cl | OMe | Me | Me |
| Me | OMe | Me | OMe | Cl | OMe | Me | OMe |
| Me | Me | H | H | Cl | Me | H | H |
| Me | Me | H | Me | Cl | Me | H | Me |
| Me | Me | H | OMe | Cl | Me | H | OMe |
| Me | Me | Me | H | Cl | Me | Me | H |
| Me | Me | Me | Me | Cl | Me | Me | Me |
| Me | Me | Me | OMe | Cl | Me | Me | OMe |
| Br | H | H | H | Br | OMe | Me | H |
| Br | H | H | Me | Br | OMe | Me | Me |
| Br | H | H | OMe | Br | OMe | Me | OMe |
| Br | OMe | H | H | Br | Me | H | H |
| Br | OMe | H | Me | Br | Me | H | Me |
| Br | OMe | H | OMe | Br | Me | H | OMe |
| Br | H | Me | H | Br | Me | Me | H |
| Br | H | Me | Me | Br | Me | Me | Me |
| Br | H | Me | OMe | Br | Me | Me | OMe |
| \multicolumn{8}{c}{$A^1$ is CH, $A^2$ is CBr, $A^3$ is N, $A^4$ is CH} ||||||||
| Me | H | H | H | Cl | H | H | H |
| Me | H | H | Me | Cl | H | H | Me |
| Me | H | H | OMe | Cl | H | H | OMe |
| Me | OMe | H | H | Cl | OMe | H | H |
| Me | OMe | H | Me | Cl | OMe | H | Me |
| Me | OMe | H | OMe | Cl | OMe | H | OMe |
| Me | H | Me | H | Cl | H | Me | H |
| Me | H | Me | Me | Cl | H | Me | Me |
| Me | H | Me | OMe | Cl | H | Me | OMe |
| Me | OMe | Me | H | Cl | OMe | Me | H |
| Mc | OMe | Me | Me | Cl | OMe | Me | Me |
| Me | OMe | Me | OMe | Cl | OMe | Me | OMe |
| Me | Me | H | H | Cl | Me | H | H |
| Me | Me | H | Me | Cl | Me | H | Me |
| Me | Me | H | OMe | Cl | Me | H | OMe |
| Me | Me | Me | H | Cl | Me | Me | H |
| Me | Me | Me | Me | Cl | Me | Me | Me |
| Me | Me | Me | OMe | Cl | Me | Me | OMe |
| Br | H | H | H | Br | OMe | Me | H |
| Br | H | H | Me | Br | OMe | Me | Me |
| Br | H | H | OMe | Br | OMe | Me | OMe |
| Br | OMe | H | H | Br | Me | H | H |
| Br | OMe | H | Me | Br | Me | H | Me |
| Br | OMe | H | OMe | Br | Me | H | OMe |
| Br | H | Me | H | Br | Me | Me | H |
| Br | H | Me | Me | Br | Me | Me | Me |
| Br | H | Me | OMe | Br | Me | Me | OMe |

TABLE 21

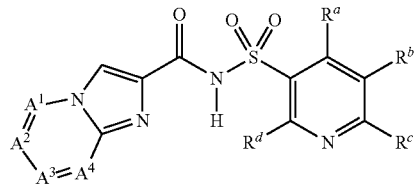

| $R^a$ | $R^b$ | $R^c$ | $R^d$ | $R^a$ | $R^b$ | $R^c$ | $R^d$ |
|---|---|---|---|---|---|---|---|
| \multicolumn{8}{c}{$A^1$ is CH, $A^2$ is CCF$_3$, $A^3$ is N, $A^4$ is CH} ||||||||
| H | H | H | H | Me | H | H | H |
| H | H | H | Me | Me | H | H | Me |
| H | H | H | CF$_3$ | Me | H | H | CF$_3$ |
| H | H | H | Cl | Me | H | H | Cl |
| H | H | H | Br | Me | H | H | Br |
| H | H | Me | H | Me | H | Me | H |
| H | H | Me | Me | Me | H | Me | Me |
| H | H | Me | CF$_3$ | Me | H | Me | CF$_3$ |
| H | H | Me | Cl | Me | H | Me | Cl |
| H | H | Me | Br | Me | H | Me | Br |
| H | Cl | H | H | Me | Cl | H | H |
| H | Cl | H | Me | Me | Cl | H | Me |
| H | Cl | H | CF$_3$ | Me | Cl | H | CF$_3$ |
| H | Cl | H | Cl | Me | Cl | H | Cl |
| H | Cl | H | Br | Me | Cl | H | Br |
| H | Cl | Me | H | Me | Cl | Me | H |
| H | Cl | Me | Me | Me | Cl | Me | Me |
| H | Cl | Me | CF$_3$ | Me | Cl | Me | CF$_3$ |
| H | Cl | Me | Cl | Me | Cl | Me | Cl |
| H | Cl | Me | Br | Me | Cl | Me | Br |
| H | Me | H | H | Me | Me | H | H |
| H | Me | H | Me | Me | Me | H | Me |
| H | Me | H | CF$_3$ | Me | Me | H | CF$_3$ |
| H | Me | H | Cl | Me | Me | H | Cl |
| H | Me | H | Br | Me | Me | H | Br |
| H | Me | Me | H | Me | Me | Me | H |
| H | Me | Me | Me | Me | Me | Me | Me |
| H | Me | Me | CF$_3$ | Me | Me | Me | CF$_3$ |
| H | Me | Me | Cl | Me | Me | Me | Cl |
| H | Me | Me | Br | Me | Me | Me | Br |
| H | CF$_3$ | H | H | Me | CF$_3$ | H | H |
| H | CF$_3$ | H | Me | Me | CF$_3$ | H | Me |
| H | CF$_3$ | H | CF$_3$ | Me | CF$_3$ | H | CF$_3$ |
| H | CF$_3$ | H | Cl | Me | CF$_3$ | H | Cl |
| H | CF$_3$ | H | Br | Me | CF$_3$ | H | Br |
| H | CF$_3$ | Me | H | Me | CF$_3$ | Me | H |
| H | CF$_3$ | Me | Me | Me | CF$_3$ | Me | Me |
| H | CF$_3$ | Me | CF$_3$ | Me | CF$_3$ | Me | CF$_3$ |
| H | CF$_3$ | Me | Cl | Me | CF$_3$ | Me | Cl |
| H | CF$_3$ | Me | Br | Me | CF$_3$ | Me | Br |
| H | OMe | H | H | Me | OMe | H | H |
| H | OMe | H | Me | Me | OMe | H | Me |
| H | OMe | H | CF$_3$ | Me | OMe | H | CF$_3$ |
| H | OMe | H | Cl | Me | OMe | H | Cl |
| H | OMe | H | Br | Me | OMe | H | Br |
| H | OMe | Me | H | Me | OMe | Me | H |
| H | OMe | Me | Me | Me | OMe | Me | Me |
| H | OMe | Me | CF$_3$ | Me | OMe | Me | CF$_3$ |
| H | OMe | Me | Cl | Me | OMe | Me | Cl |
| H | OMe | Me | Br | Me | OMe | Me | Br |
| \multicolumn{8}{c}{$A^1$ is CH, $A^2$ is CBr, $A^3$ is N, $A^4$ is CH} ||||||||
| H | H | H | H | Me | H | H | H |
| H | H | H | Me | Me | H | H | Me |
| H | H | H | CF$_3$ | Me | H | H | CF$_3$ |
| H | H | H | Cl | Me | H | H | Cl |
| H | H | H | Br | Me | H | H | Br |
| H | H | Me | H | Me | H | Me | H |
| H | H | Me | Me | Me | H | Me | Me |
| H | H | Me | CF$_3$ | Me | H | Me | CF$_3$ |
| H | H | Me | Cl | Me | H | Me | Cl |
| H | H | Me | Br | Me | H | Me | Br |
| H | Cl | H | H | Me | Cl | H | H |
| H | Cl | H | Me | Me | Cl | H | Me |
| H | Cl | H | CF$_3$ | Me | Cl | H | CF$_3$ |
| H | Cl | H | Cl | Me | Cl | H | Cl |

TABLE 21-continued (structure: imidazole carboxamide sulfonamide pyridine with A¹, A², A³, A⁴ positions and Rᵃ, Rᵇ, Rᶜ, Rᵈ substituents)

| Rᵃ | Rᵇ | Rᶜ | Rᵈ | Rᵃ | Rᵇ | Rᶜ | Rᵈ |
|----|----|----|----|----|----|----|----|
| H | Cl | H | Br | Me | Cl | H | Br |
| H | Cl | Me | H | Me | Cl | Me | H |
| H | Cl | Me | Me | Me | Cl | Me | Me |
| H | Cl | Me | CF₃ | Me | Cl | Me | CF₃ |
| H | Cl | Me | Cl | Me | Cl | Me | Cl |
| H | Cl | Me | Br | Me | Cl | Me | Br |
| H | Me | H | H | Me | Me | H | H |
| H | Me | H | Me | Me | Me | H | Me |
| H | Me | H | CF₃ | Me | Me | H | CF₃ |
| H | Me | H | Cl | Me | Me | H | Cl |
| H | Me | H | Br | Me | Me | H | Br |
| H | Me | Me | H | Me | Me | Me | H |
| H | Me | Me | Me | Me | Me | Me | Me |
| H | Me | Me | CF₃ | Me | Me | Me | CF₃ |
| H | Me | Me | Cl | Me | Me | Me | Cl |
| H | Me | Me | Br | Me | Me | Me | Br |
| H | CF₃ | H | H | Me | CF₃ | H | H |
| H | CF₃ | H | Me | Me | CF₃ | H | Me |
| H | CF₃ | H | CF₃ | Me | CF₃ | H | CF₃ |
| H | CF₃ | H | Cl | Me | CF₃ | H | Cl |
| H | CF₃ | H | Br | Me | CF₃ | H | Br |
| H | CF₃ | Me | H | Me | CF₃ | Me | H |
| H | CF₃ | Me | Me | Me | CF₃ | Me | Me |
| H | CF₃ | Me | CF₃ | Me | CF₃ | Me | CF₃ |
| H | CF₃ | Me | Cl | Me | CF₃ | Me | Cl |
| H | CF₃ | Me | Br | Me | CF₃ | Me | Br |
| H | OMe | H | H | Me | OMe | H | H |
| H | OMe | H | Me | Me | OMe | H | Me |
| H | OMe | H | CF₃ | Me | OMe | H | CF₃ |
| H | OMe | H | Cl | Me | OMe | H | Cl |
| H | OMe | H | Br | Me | OMe | H | Br |
| H | OMe | Me | H | Me | OMe | Me | H |
| H | OMe | Me | Me | Me | OMe | Me | Me |
| H | OMe | Me | CF₃ | Me | OMe | Me | CF₃ |
| H | OMe | Me | Cl | Me | OMe | Me | Cl |
| H | OMe | Me | Br | Me | OMe | Me | Br |

TABLE 22

(structure similar with A¹, A², A³, A⁴ defined below)

| Rᵃ | Rᵇ | Rᶜ | Rᵈ | Rᵃ | Rᵇ | Rᶜ | Rᵈ |
|----|----|----|----|----|----|----|----|
| A¹ is CH, A² is CCF₃, A³ is N, A⁴ is CH ||||||||
| H | H | H | H | Me | H | H | H |
| H | H | H | Me | Me | H | H | Me |
| H | H | H | Cl | Me | H | H | Cl |
| H | H | Me | H | Me | H | Me | H |
| H | H | Me | Me | Me | H | Me | Me |
| H | H | Me | Cl | Me | H | Me | Cl |
| A¹ is CH, A² is CBr, A³ is N, A⁴ is CH ||||||||
| H | H | H | H | Me | H | H | H |
| H | H | H | Me | Me | H | H | Me |
| H | H | H | Cl | Me | H | H | Cl |
| H | H | Me | H | Me | H | Me | H |
| H | H | Me | Me | Me | H | Me | Me |
| H | H | Me | Cl | Me | H | Me | Cl |

A compound of this invention will generally be used as a parasitic nematode control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspo-emulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |

|  | Weight Percent | | |
| --- | --- | --- | --- |
|  | Active Ingredient | Diluent | Surfactant |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkypyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual international and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A and B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| compound 1 | 98.5% |
| silica aerogel | 0.5% |
| synthetic amorphous fine silica | 1.0% |

Example B

| Wettable Powder | |
|---|---|
| compound 4 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| compound 6 | 10.0% |
| attapulgite granules (low volatile matter, 0.71/0.30 mm; U.S.S. No. 25-50 sieves) | 90.0% |

Example D

| Extruded Pellet | |
|---|---|
| compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| compound 4 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| compound 6 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| compound 4 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
|---|---|
| compound 6 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| compound 4 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| compound 6 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

These present compounds and compositions are thus useful agronomically for protecting field crops from parasitic nematodes, and also nonagronomically for protecting other horticultural crops and plants from phytophagous parasitic nematodes. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the parasitic nematode control effectiveness of the present compounds and compositions. In particular, the present compounds and compositions may interact synergistically with the phenotypic expression of proteins or other natural products toxic to parasitic nematodes to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Compounds of this invention can exhibit activity against a wide spectrum of parasitic nematodes that live or grow inside or feed on plants (e.g., foliage, fruit, stems, roots or seeds) or animals and humans (e.g., vascular or digestive systems or other tissues) and therefore damage growing and stored agronomic crops, forestry, greenhouse crops, ornamentals and nursery crops, or afflict animal and human health. Crops of particular interest are fruiting vegetables such as solanaceous and cucurbit crops, plantation crops such as banana and coffee, root crops such as potatoes, onion and carrots, and field crops such as tobacco, peanut, cotton, sugarcane and soybean.

Compounds of the present invention can have activity on parasitic helminths of the phylum Platyhelminthes (flatworms), including the classes Cestoda (tapeworms) and Trematoda (flukes), the phylum Acanthocephala (thorny-headed worms), including the classes Archiacanthocephala and Palaeacanthocephala, the phylum Nematoda (roundworms), including the classes Adenophorea (Aphasmidae) and Secernentea (Plasmidae), and the orders Enoplida (whipworms), Dorylaimida, Rhabdidita (free-living worms), Strongylida (hookworms and lungworms), Ascaridida (intestinal roundworms), Oxyurida (pinworms), Spirurida (filarial nematodes), Tylenchida, Aphelenchida, Diplogasterida, Rhabdiasida and Camallanida.

Compounds of the present invention can have activity on economically important parasitic nematodes including, but not limited to, root-knot nematodes of the genus *Meloidogyne*, cyst nematodes of the genera *Heterodera* and *Globodera*, lesion nematodes of the genus *Pratylenchus*, reniform nematodes of the genus *Rotylenchulus*, burrowing nematodes of the genus *Radopholus*, sting nematodes of the genus *Belonolaimus*, spiral nematodes of the genera *Helicotylenchus* and *Scutellonema*, citrus nematodes of the genus *Tylenchulus*, stubby root nematodes of the genera *Trichodorus* and *Paratrichodorus*, dagger nematodes of the genus *Xiphinema*, stunt nematodes of the genus *Tylenchorhynchus*, needle nematodes of the genera *Longidorus* and *Paralongidorus*, lance nematodes of the genus *Hoplolaimus*, ring nematodes of the family Criconematidae, stem nematodes of the genera *Ditylenchus* and *Anguina*, and foliar/stem nematodes of the genera *Aphelenchoides* and *Rhadinaphelenchus*.

Compounds of the present invention can also have activity on animal and human health parasites including, but not limited to, roundworms such as *Strongylus vulgaris* in horses, *Toxocara canis* in dogs, *Haemonchus contortus* in sheep and *Dirofilaria immitis* in dogs, and flukes and tapeworms such as *Anoplocephala perfliata* in horses and *Fasciola hepatica* in ruminants.

Of note is use of compounds of this invention for controlling southern root-knot nematode (*Meloidogyne incognita*). Those skilled in the art will appreciate that not all compounds are equally effective against all growth stages of all nematodes.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a compound of Formula 1, an N-oxide, or salt thereof, and an effective amount of at least one additional biologically active compound or agent and can further comprise at least one of surfactants, solid diluents or liquid diluents. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, buprofezin, cadusafos, carbaryl, cartap, chlorantraniliprole, chiorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPTII® bioinsecticides prepared by the CellCap® process (CellCap®, MVP® and MVPII® are trademarks of Mycogen Corporation, Indianapolis, Ind., USA); entomopathogenic fingi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism with invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2$^{nd}$ Edition*, L. G. Copping, Ed., British Crop Protection Council, Farnham, Surrey, U.K., 2001.

For embodiments where one or more of these various mixing partners are used, the weight ratio of these various mixing partners (in total) to a compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of parasitic nematodes controlled beyond the spectrum controlled by a compound of Formula 1 alone.

Table A lists specific combinations of a compound of Formula 1 with other invertebrate pest control agents illustrative of the mixtures, compositions and methods of the present invention and includes additional embodiments of weight ratio ranges for application rates. The first column of Table A lists the specific invertebrate control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1 (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |

TABLE A-continued

| Invertebrate Pest Control Agent | Mode of Action or Chemical Class | Typical Weight Ratio |
|---|---|---|
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the invertebrate pest control agents listed in Table A above.

The weight ratios of a compound of Formula 1, an N-oxide, or a salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a compound of Formula 1 (compound numbers (Cmpd. No.) refer to compounds in Index Table A) and an additional invertebrate pest control agent.

TABLE B

| Mixture No. | Cmpd. No. | and | Invertebrate Pest Control Agent | Mixture No. | Cmpd. No. | and | Invertebrate Pest Control Agent |
|---|---|---|---|---|---|---|---|
| B1-1 | 1 | and | Abamectin | B1-36 | 1 | and | Imidacloprid |
| B1-2 | 1 | and | Acetamiprid | B1-37 | 1 | and | Indoxacarb |
| B1-3 | 1 | and | Amitraz | B1-38 | 1 | and | Lambda-cyhalothrin |
| B1-4 | 1 | and | Avermectin | B1-39 | 1 | and | Lufenuron |
| B1-5 | 1 | and | Azadirachtin | B1-40 | 1 | and | Metaflumizone |
| B1-5a | 1 | and | Bensultap | B1-41 | 1 | and | Methomyl |
| B1-6 | 1 | and | Beta-cyfluthrin | B1-42 | 1 | and | Methoprene |
| B1-7 | 1 | and | Bifenthrin | B1-43 | 1 | and | Methoxyfenozide |
| B1-8 | 1 | and | Buprofezin | B1-44 | 1 | and | Nitenpyram |
| B1-9 | 1 | and | Cartap | B1-45 | 1 | and | Nithiazine |
| B1-10 | 1 | and | Chlorantraniliprole | B1-46 | 1 | and | Novaluron |
| B1-11 | 1 | and | Chlorfenapyr | B1-47 | 1 | and | Oxamyl |
| B1-12 | 1 | and | Chlorpyrifos | B1-48 | 1 | and | Phosmet |
| B1-13 | 1 | and | Clothianidin | B1-49 | 1 | and | Pymetrozine |
| B1-14 | 1 | and | Cyantraniliprole | B1-50 | 1 | and | Pyrethrin |
| B1-15 | 1 | and | Cyfluthrin | B1-51 | 1 | and | Pyridaben |
| B1-16 | 1 | and | Cyhalothrin | B1-52 | 1 | and | Pyridalyl |
| B1-17 | 1 | and | Cypermethrin | B1-53 | 1 | and | Pyriproxyfen |
| B1-18 | 1 | and | Cyromazine | B1-54 | 1 | and | Ryanodine |
| B1-19 | 1 | and | Deltamethrin | B1-55 | 1 | and | Spinetoram |
| B1-20 | 1 | and | Dieldrin | B1-56 | 1 | and | Spinosad |
| B1-21 | 1 | and | Dinotefuran | B1-57 | 1 | and | Spirodiclofen |
| B1-22 | 1 | and | Diofenolan | B1-58 | 1 | and | Spiromesifen |
| B1-23 | 1 | and | Emamectin | B1-59 | 1 | and | Spirotetramat |
| B1-24 | 1 | and | Endosulfan | B1-60 | 1 | and | Tebufenozide |
| B1-25 | 1 | and | Esfenvalerate | B1-61 | 1 | and | Thiacloprid |
| B1-26 | 1 | and | Ethiprole | B1-62 | 1 | and | Thiamethoxam |
| B1-27 | 1 | and | Fenothiocarb | B1-63 | 1 | and | Thiodicarb |
| B1-28 | 1 | and | Fenoxycarb | B1-64 | 1 | and | Thiosultap-sodium |
| B1-29 | 1 | and | Fenvalerate | B1-65 | 1 | and | Tolfenpyrad |
| B1-30 | 1 | and | Fipronil | B1-66 | 1 | and | Tralomethrin |
| B1-31 | 1 | and | Flonicamid | B1-67 | 1 | and | Triazamate |
| B1-32 | 1 | and | Flubendiamide | B1-68 | 1 | and | Triflumuron |
| B1-33 | 1 | and | Flufenoxuron | B1-69 | 1 | and | *Bacillus thuringiensis* |
| B1-34 | 1 | and | Hexaflumuron | B1-70 | 1 | and | *Bacillus thuringiensis* delta-endotoxin |
| B1-35 | 1 | and | Hydramethylnon | B1-71 | 1 | and | NPV (e.g., Gemstar) |
| B2-1 | 4 | and | Abamectin | B2-36 | 4 | and | Imidacloprid |
| B2-2 | 4 | and | Acetamiprid | B2-37 | 4 | and | Indoxacarb |
| B2-3 | 4 | and | Amitraz | B2-38 | 4 | and | Lambda-cyhalothrin |
| B2-4 | 4 | and | Avermectin | B2-39 | 4 | and | Lufenuron |
| B2-5 | 4 | and | Azadirachtin | B2-40 | 4 | and | Metaflumizone |
| B2-5a | 4 | and | Bensultap | B2-41 | 4 | and | Methomyl |
| B2-6 | 4 | and | Beta-cyfluthrin | B2-42 | 4 | and | Methoprene |
| B2-7 | 4 | and | Bifenthrin | B2-43 | 4 | and | Methoxyfenozide |
| B2-8 | 4 | and | Buprofezin | B2-44 | 4 | and | Nitenpyram |
| B2-9 | 4 | and | Cartap | B2-45 | 4 | and | Nithiazine |
| B2-10 | 4 | and | Chlorantraniliprole | B2-46 | 4 | and | Novaluron |
| B2-11 | 4 | and | Chlorfenapyr | B2-47 | 4 | and | Oxamyl |
| B2-12 | 4 | and | Chlorpyrifos | B2-48 | 4 | and | Phosmet |
| B2-13 | 4 | and | Clothianidin | B2-49 | 4 | and | Pymetrozine |
| B2-14 | 4 | and | Cyantraniliprole | B2-50 | 4 | and | Pyrethrin |
| B2-15 | 4 | and | Cyfluthrin | B2-51 | 4 | and | Pyridaben |
| B2-16 | 4 | and | Cyhalothrin | B2-52 | 4 | and | Pyridalyl |
| B2-17 | 4 | and | Cypermethrin | B2-53 | 4 | and | Pyriproxyfen |
| B2-18 | 4 | and | Cyromazine | B2-54 | 4 | and | Ryanodine |
| B2-19 | 4 | and | Deltamethrin | B2-55 | 4 | and | Spinetoram |
| B2-20 | 4 | and | Dieldrin | B2-56 | 4 | and | Spinosad |
| B2-21 | 4 | and | Dinotefuran | B2-57 | 4 | and | Spirodiclofen |

TABLE B-continued

| Mixture No. | Cmpd. No. | and | Invertebrate Pest Control Agent | Mixture No. | Cmpd. No. | and | Invertebrate Pest Control Agent |
|---|---|---|---|---|---|---|---|
| B2-22 | 4 | and | Diofenolan | B2-58 | 4 | and | Spiromesifen |
| B2-23 | 4 | and | Emamectin | B2-59 | 4 | and | Spirotetramat |
| B2-24 | 4 | and | Endosulfan | B2-60 | 4 | and | Tebufenozide |
| B2-25 | 4 | and | Esfenvalerate | B2-61 | 4 | and | Thiacloprid |
| B2-26 | 4 | and | Ethiprole | B2-62 | 4 | and | Thiamethoxam |
| B2-27 | 4 | and | Fenothiocarb | B2-63 | 4 | and | Thiodicarb |
| B2-28 | 4 | and | Fenoxycarb | B2-64 | 4 | and | Thiosultap-sodium |
| B2-29 | 4 | and | Fenvalerate | B2-65 | 4 | and | Tolfenpyrad |
| B2-30 | 4 | and | Fipronil | B2-66 | 4 | and | Tralomethrin |
| B2-31 | 4 | and | Flonicamid | B2-67 | 4 | and | Triazamate |
| B2-32 | 4 | and | Flubendiamide | B2-68 | 4 | and | Triflumuron |
| B2-33 | 4 | and | Flufenoxuron | B2-69 | 4 | and | *Bacillus thuringiensis* |
| B2-34 | 4 | and | Hexaflumuron | B2-70 | 4 | and | *Bacillus thuringiensis* delta-endotoxin |
| B2-35 | 4 | and | Hydramethylnon | B2-71 | 4 | and | NPV (e.g., Gemstar) |
| B3-1 | 6 | and | Abamectin | B3-36 | 6 | and | Imidacloprid |
| B3-2 | 6 | and | Acetamiprid | B3-37 | 6 | and | Indoxacarb |
| B3-3 | 6 | and | Amitraz | B3-38 | 6 | and | Lambda-cyhalothrin |
| B3-4 | 6 | and | Avermectin | B3-39 | 6 | and | Lufenuron |
| B3-5 | 6 | and | Azadirachtin | B3-40 | 6 | and | Metaflumizone |
| B3-5a | 6 | and | Bensultap | B3-41 | 6 | and | Methomyl |
| B3-6 | 6 | and | Beta-cyfluthrin | B3-42 | 6 | and | Methoprene |
| B3-7 | 6 | and | Bifenthrin | B3-43 | 6 | and | Methoxyfenozide |
| B3-8 | 6 | and | Buprofezin | B3-44 | 6 | and | Nitenpyram |
| B3-9 | 6 | and | Cartap | B3-45 | 6 | and | Nithiazine |
| B3-10 | 6 | and | Chlorantraniliprole | B3-46 | 6 | and | Novaluron |
| B3-11 | 6 | and | Chlorfenapyr | B3-47 | 6 | and | Oxamyl |
| B3-12 | 6 | and | Chlorpyrifos | B3-48 | 6 | and | Phosmet |
| B3-13 | 6 | and | Clothianidin | B3-49 | 6 | and | Pymetrozine |
| B3-14 | 6 | and | Cyantraniliprole | B3-50 | 6 | and | Pyrethrin |
| B3-15 | 6 | and | Cyfluthrin | B3-51 | 6 | and | Pyridaben |
| B3-16 | 6 | and | Cyhalothrin | B3-52 | 6 | and | Pyridalyl |
| B3-17 | 6 | and | Cypermethrin | B3-53 | 6 | and | Pyriproxyfen |
| B3-18 | 6 | and | Cyromazine | B3-54 | 6 | and | Ryanodine |
| B3-19 | 6 | and | Deltamethrin | B3-55 | 6 | and | Spinetoram |
| B3-20 | 6 | and | Dieldrin | B3-56 | 6 | and | Spinosad |
| B3-21 | 6 | and | Dinotefuran | B3-57 | 6 | and | Spirodiclofen |
| B3-22 | 6 | and | Diofenolan | B3-58 | 6 | and | Spiromesifen |
| B3-23 | 6 | and | Emamectin | B3-59 | 6 | and | Spirotetramat |
| B3-24 | 6 | and | Endosulfan | B3-60 | 6 | and | Tebufenozide |
| B3-25 | 6 | and | Esfenvalerate | B3-61 | 6 | and | Thiacloprid |
| B3-26 | 6 | and | Ethiprole | B3-62 | 6 | and | Thiamethoxam |
| B3-27 | 6 | and | Fenothiocarb | B3-63 | 6 | and | Thiodicarb |
| B3-28 | 6 | and | Fenoxycarb | B3-64 | 6 | and | Thiosultap-sodium |
| B3-29 | 6 | and | Fenvalerate | B3-65 | 6 | and | Tolfenpyrad |
| B3-30 | 6 | and | Fipronil | B3-66 | 6 | and | Tralomethrin |
| B3-31 | 6 | and | Flonicamid | B3-67 | 6 | and | Triazamate |
| B3-32 | 6 | and | Flubendiamide | B3-68 | 6 | and | Triflumuron |
| B3-33 | 6 | and | Flufenoxuron | B3-69 | 6 | and | *Bacillus thuringiensis* |
| B3-34 | 6 | and | Hexaflumuron | B3-70 | 6 | and | *Bacillus thuringiensis* delta-endotoxin |
| B3-35 | 6 | and | Hydramethylnon | B3-71 | 6 | and | NPV (e.g., Gemstar) |

The specific mixtures listed in Table B typically combine a compound of Formula 1 with the other invertebrate pest agent in the ratios specified in Table A.

Listed below in Table C are embodiments of specific compositions comprising a compound of Formula 1 (compound numbers (Cmpd. No.) refer to compounds in Index Table A) and an additional fungicide.

TABLE C

| Mixture No. | Cmpd. No. | and | Fungicide | Mixture No. | Cmpd. No. | and | Fungicide |
|---|---|---|---|---|---|---|---|
| C1-1 | 1 | and | Probenazole | C1-17 | 1 | and | Difenoconazole |
| C1-2 | 1 | and | Tiadinil | C1-18 | 1 | and | Cyproconazole |
| C1-3 | 1 | and | Isotianil | C1-19 | 1 | and | Propiconazole |
| C1-4 | 1 | and | Pyroquilon | C1-20 | 1 | and | Fenoxanil |
| C1-5 | 1 | and | Metominostrobin | C1-21 | 1 | and | Ferimzone |
| C1-6 | 1 | and | Flutolanil | C1-22 | 1 | and | Fthalide |
| C1-7 | 1 | and | Validamycin | C1-23 | 1 | and | Kasugamycin |

TABLE C-continued

| Mixture No. | Cmpd. No. | and | Fungicide | Mixture No. | Cmpd. No. | and | Fungicide |
|---|---|---|---|---|---|---|---|
| C1-8 | 1 | and | Furametpyr | C1-24 | 1 | and | Picoxystrobin |
| C1-9 | 1 | and | Pencycuron | C1-25 | 1 | and | Penthiopyrad |
| C1-10 | 1 | and | Simeconazole | C1-26 | 1 | and | Famoxadone |
| C1-11 | 1 | and | Orysastrobin | C1-27 | 1 | and | Cymoxanil |
| C1-12 | 1 | and | Trifloxystrobin | C1-28 | 1 | and | Proquinazid |
| C1-13 | 1 | and | Isoprothiolane | C1-29 | 1 | and | Flusilazole |
| C1-14 | 1 | and | Azoxystrobin | C1-30 | 1 | and | Mancozeb |
| C1-15 | 1 | and | Tricyclazole | C1-31 | 1 | and | Copper hydroxide |
| C1-16 | 1 | and | Hexaconazole | C1-32 | 1 | and | (a) |
| C2-1 | 4 | and | Probenazole | C2-17 | 4 | and | Difenoconazole |
| C2-2 | 4 | and | Tiadinil | C2-18 | 4 | and | Cyproconazole |
| C2-3 | 4 | and | Isotianil | C2-19 | 4 | and | Propiconazole |
| C2-4 | 4 | and | Pyroquilon | C2-20 | 4 | and | Fenoxanil |
| C2-5 | 4 | and | Metominostrobin | C2-21 | 4 | and | Ferimzone |
| C2-6 | 4 | and | Flutolanil | C2-22 | 4 | and | Fthalide |
| C2-7 | 4 | and | Validamycin | C2-23 | 4 | and | Kasugamycin |
| C2-8 | 4 | and | Furametpyr | C2-24 | 4 | and | Picoxystrobin |
| C2-9 | 4 | and | Pencycuron | C2-25 | 4 | and | Penthiopyrad |
| C2-10 | 4 | and | Simeconazole | C2-26 | 4 | and | Famoxadone |
| C2-11 | 4 | and | Orysastrobin | C2-27 | 4 | and | Cymoxanil |
| C2-12 | 4 | and | Trifloxystrobin | C2-28 | 4 | and | Proquinazid |
| C2-13 | 4 | and | Isoprothiolane | C2-29 | 4 | and | Flusilazole |
| C2-14 | 4 | and | Azoxystrobin | C2-30 | 4 | and | Mancozeb |
| C2-15 | 4 | and | Tricyclazole | C2-31 | 4 | and | Copper hydroxide |
| C2-16 | 4 | and | Hexaconazole | C2-32 | 4 | and | (a) |
| C3-1 | 6 | and | Probenazole | C3-17 | 6 | and | Difenoconazole |
| C3-2 | 6 | and | Tiadinil | C3-18 | 6 | and | Cyproconazole |
| C3-3 | 6 | and | Isotianil | C3-19 | 6 | and | Propiconazole |
| C3-4 | 6 | and | Pyroquilon | C3-20 | 6 | and | Fenoxanil |
| C3-5 | 6 | and | Metominostrobin | C3-21 | 6 | and | Ferimzone |
| C3-6 | 6 | and | Flutolanil | C3-22 | 6 | and | Fthalide |
| C3-7 | 6 | and | Validamycin | C3-23 | 6 | and | Kasugamycin |
| C3-8 | 6 | and | Furametpyr | C3-24 | 6 | and | Picoxystrobin |
| C3-9 | 6 | and | Pencycuron | C3-25 | 6 | and | Penthiopyrad |
| C3-10 | 6 | and | Simeconazole | C3-26 | 6 | and | Famoxadone |
| C3-11 | 6 | and | Orysastrobin | C3-27 | 6 | and | Cymoxanil |
| C3-12 | 6 | and | Trifloxystrobin | C3-28 | 6 | and | Proquinazid |
| C3-13 | 6 | and | Isoprothiolane | C3-29 | 6 | and | Flusilazole |
| C3-14 | 6 | and | Azoxystrobin | C3-30 | 6 | and | Mancozeb |
| C3-15 | 6 | and | Tricyclazole | C3-31 | 6 | and | Copper hydroxide |
| C3-16 | 6 | and | Hexaconazole | C3-32 | 6 | and | (a) |

(a)  1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Parasitic nematodes are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling a parasitic nematode in agronomic and/or nonagronomic applications, comprising contacting the parasitic nematode or its environment with a biologically effective amount of one or more of the compounds of the invention, or with a composition comprising at least one such compound or a composition comprising at least one such compound and at least one additional biologically active compound or agent. Examples of suitable compositions comprising a compound of the invention and at least one additional biologically active compound or agent include granular compositions wherein the additional active compound is present on the same granule as the compound of the invention or on granules separate from those of the compound of the invention.

To achieve contact with a compound or composition of the invention to protect a field crop from parasitic nematodes, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling a parasitic nematode comprising contacting the parasitic nematode or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact involves a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from parasitic nematodes. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples of genetically transformed plants include those expressing proteins toxic to parasitic nematodes, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide, or salt thereof, and a film former or adhesive agent. Seed can be coated by spraying a flowable suspension concentrate directly into a tumbling bed of seeds and then drying the seeds. Alternatively, other formulation types such as wetted powders, solutions, suspo-emulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Mongraph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

For agronomic applications, the rate of application required for effective control (i.e. "biologically effective amount") will depend on such factors as the species of nematode to be controlled, the nematode's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control nematodes in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of parasitic nematode control.

The compounds of this invention prepared by the methods described herein are shown in Index Tables A and B. The following abbreviations are used in the index Tables which follow: Cmpd means Compound. The variable "R" represents one or a combination of substituents as listed in the Index Tables. The abbreviation "Ex." stands for "Example" and is followed by a number indicating in which Synthesis Example the compound is prepared.

INDEX TABLE A

| Cmpd | $A^1$ | $A^2$ | $A^3$ | $A^4$ | R | m.p. (° C.) |
|---|---|---|---|---|---|---|
| 1 (Ex. 3) | CH | $CCF_3$ | N | CH | 2-chloro, 5-methoxy | 238-237 |
| 2 | CH | CH | CH | N | 2-chloro, 5-methoxy | 213-214 |
| 3 | CH | CH | CH | N | 2-chloro, 5-trifluoromethyl | 214-215 |
| 4 (Ex. 1) | CH | CBr | CH | N | 2-chloro, 5-trifluoromethyl | >250 |
| 5 | CH | $CCF_3$ | CH | N | 2,5-dimethyl, 4-cyano | 212-213 |
| 6 (Ex. 2) | CH | $CCF_3$ | CH | N | 2-chloro, 5-trifluoromethyl | 211-212 |
| 7 | CH | $CCF_3$ | CH | N | 2-chloro, 5-methoxy | 221-222 |
| 8 | CH | CBr | CH | N | 2-chloro, 5-methoxy | 211-212 |
| 9 | CH | CBr | CH | N | 2,5-dimethyl, 4-cyano | >250 |
| 10 | CH | CBr | CH | N | 2-bromo, 5-trifluoromethyl | >250 |
| 11 | CH | $CCF_3$ | N | CH | 2,5-dimethyl | 277-280 |
| 12 | CH | $CCF_3$ | N | CH | 2-chloro, 5-trifluoromethyl | 217-219 |
| 13 | CH | $CCF_3$ | N | Cl | 2-chloro, 5-trifluoromethyl | 125-127 |
| 14 | CH | $CCF_3$ | N | Cl | 2-chloro, 5-methoxy | 196-199 |

INDEX TABLE B

| Cmpd | $A^1$ | $A^2$ | $A^3$ | $A^4$ | Q | m.p. (° C.) |
|---|---|---|---|---|---|---|
| 15 | CH | CBr | CH | N | 3-methyl-2-thienyl | 233-234 |

$R^2$ is H

The following Tests demonstrate the control efficacy of compounds of this invention on specific pests. "Control efficacy" represents inhibition of parasitic nematode development (including mortality) that causes significantly reduced feeding. The pest control protection afforded by the compounds is not limited, however, to these species.

Biological Examples of the Invention

Test A

Control of the southern root-knot nematode (*Meloidogyne incognita*) through contact and/or systemic means was evaluated in test units consisting of small open containers filled with a sandy soil mixture and cucumber seedlings.

Test compounds were formulated using a solution containing 50% acetone and 50% water. Test compounds were applied directly to the soil of the test units at a concentration of 250 ppm active ingredient. Each test was replicated 3 times. After treatment, the test units were allowed to dry for 1 hour, after which time about 250 second-stage juvenile (J2) larvae were pipetted into the soil. The test units were held at 27° C. and watered as needed for 7 days.

Nematocidal efficacy was determined by the amount of root gall formation observed when compared to an untreated control. No gall formation was indicative of 100% nematode control. Gall formation equivalent to that found in the untreated control was indicative of 0% control. No nematode control rating was given to compounds showing significant phytotoxicity.

Of the compounds tested at a concentration of 250 ppm, the following provided good levels of plant protection (50% or more reduction in root galling, compared to solvent-treated controls) and exhibited no significant phytotoxicity: 1, 4, 6, 11 and 12.

What is claimed is:

1. A compound selected from Formula 1, an N-oxide, or a salt thereof,

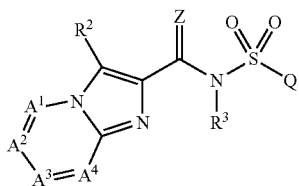

1 wherein

Z is O or S;

$A^1$, $A^3$ and $A^4$ are independently N or $CR^1$, provided that only one of $A^1$, $A^3$ and $A^4$ must be N in each compound;

$A^2$ is $C-CF_3$;

each $R^1$ is independently H, halogen, cyano, nitro, $OR^4$, $NR^5R^6$, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_3-C_7$ cycloalkyl, $C(X)R^7$, $C(O)OR^8$, $C(O)NR^{11}R^{12}$, $S(O)_mR^9$ or $S(O)_2NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1-C_4$ alkyl, $C_2-C_4$ alkenyl, $C_2-C_4$ alkynyl, $C_1-C_4$ haloalkyl, $C_2-C_4$ haloalkenyl, $C(X)R^7$, $C(O)OR^8$, $C(O)NR^{11}R^{12}$, $S(O)_mR^9$ and $S(O)_2NR^{11}R^{12}$;

$R^2$ is H, halogen, cyano, nitro, $OR^4$, $NR^5R^6$, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_3-C_7$ cycloalkyl, $C(X)R^7$, $C(O)OR^8$, $C(O)NR^{11}R^{12}$, $S(O)_mR^9$ or $S(O)_2NR^{11}R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1-C_4$ alkyl, $C_2-C_4$ alkenyl, $C_2-C_4$ alkynyl, $C_1-C_4$ haloalkyl, $C_2-C_4$ haloalkenyl, $C(X)R^7$, $C(O)OR^8$, $C(O)NR^{11}R^{12}$, $S(O)_mR^9$ and $S(O)_2NR^{11}R^{12}$;

$R^3$ is H, $C(X)R^7$, $C(O)OR^8$, $C(O)NR^{11}R^{12}$, $S(O)_mR^9$ or $S(O)_2NR^{11}R^{12}$; or $C_1-C_6$ alkyl, $C_2-C_6$ alkenyl, $C_2-C_6$ alkynyl, $C_3-C_7$ cycloalkyl, $C_4-C_8$ cycloalkylalkyl or $C_5-C_7$ cycloalkenyl, each optionally substituted with 1 to 4 substituents independently selected from the group consisting of halogen, cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$; or $C_1-C_6$ alkyl substituted with 1 or 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1-C_4$ alkyl, $C_2-C_4$ alkenyl, $C_2-C_4$ alkynyl, $C_1-C_4$ haloalkyl, $C_2-C_4$ haloalkenyl, $C_2-C_6$ alkoxyalkyl, $C(X)R^7$, $C(O)OR^8$, $C(O)NR^{11}R^{12}$, $S(O)_mR^9$ and $S(O)_2NR^{11}R^{12}$;

Q is phenyl, naphthalenyl, a 5- or 6-membered heteroaromatic ring or an 8- to 10-membered aromatic bicyclic ring system, each optionally substituted with 1 to 5 substituents independently selected from the group consisting of halogen, cyano, nitro, $OR^4$, $NR^5R^6$, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

each X is independently O or S;

each $R^4$ is independently H, $NR^{5a}R^{6a}$, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C(X)R^7$, $C(O)OR^8$, $C(O)NR^{11}R^{12}$ or $S(O)_mR^9$; or $C_3-C_7$ cycloalkyl, $C_4-C_8$ cycloalkylalkyl, $C_6-C_{14}$ cycloalkylcycloalkyl or $C_5-C_7$ cycloalkenyl, each optionally substituted with 1 to 4 substituents independently selected from the group consisting of halogen, cyano, nitro, $C_1-C_4$ alkyl, $C_1-C_4$ haloalkyl, $OR^{4a}$ and $S(O)_mR^{9a}$; or phenyl optionally substituted with 1 to 3 substituents independently selected from the group consisting of halogen, cyano, nitro, $C_1-C_4$ alkyl, $C_2-C_4$ alkenyl, $C_2-C_4$ alkynyl, $C_1-C_4$ haloalkyl, $C_2-C_4$ haloalkenyl, $C(X)R^{7a}$, $C(O)OR^{8a}$, $C(O)NR^{11}R^{12}$, $OR^{4a}$, $C_2-C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{4a}$ is independently H, $C_1-C_6$ alkyl or $C_1-C_6$ haloalkyl;

each $R^5$ is independently H, $NR^{5a}R^{6a}$, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C(X)R^7$, $C(O)OR^8$, $C(O)NR^{11}R^{12}$, $S(O)_mR^9$ or $S(O)_2NR^{11}R^{12}$; or $C_3-C_7$ cycloalkyl, $C_4-C_8$ cycloalkylalkyl, $C_6-C_{14}$ cycloalkylcycloalkyl or $C_5-C_7$ cycloalkenyl, each optionally substituted with 1 to 4 substituents independently selected from the group consisting of halogen, cyano, nitro, $C_1-C_4$ alkyl, $C_1-C_4$ haloalkyl, $OR^{4a}$ and $S(O)_mR^{9a}$; or phenyl optionally substituted with 1 to 3 substituents independently selected from the group consisting of halogen, cyano, nitro, $C_1-C_4$ alkyl, $C_2-C_4$ alkenyl, $C_2-C_4$ alkynyl, $C_1-C_4$ haloalkyl, $C_2-C_4$ haloalkenyl, $C(X)R^{7a}$, $C(O)OR^{8a}$, $C(O)NR^{11}R^{12}$, $OR^{4a}$, $C_2-C_6$ alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1-C_6$ alkyl;

each $R^6$ is independently H, $C_1-C_6$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_3-C_7$ cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{6a}$ is independently H, $C_1-C_6$ alkyl, $C(O)R^{13}$ or $C(O)OR^{13}$;

each $R^7$ is independently H, $C_1-C_6$ alkyl, $C_1-C_6$ haloalkyl, $C_2-C_6$ alkenyl, $C_2-C_6$ haloalkenyl, $C_2-C_6$ alkynyl or $C_2-C_6$ haloalkynyl; or $C_3-C_7$ cycloalkyl, $C_4-C_8$ cycloalkylalkyl, $C_6-C_{14}$ cycloalkylcycloalkyl or $C_5-C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_m R^{9a}$, $S(O)_2 NR^{11} R^{12}$, $NR^{5a} R^{6a}$, $OC(O)R^{7a}$ and $N(R^{10})C(O)R^{7a}$;

each $R^{7a}$ is independently $C_1$-$C_6$ alkyl or $C_1$-$C_6$ haloalkyl;

each $R^8$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_m R^{9a}$, $S(O)_2 NR^{11} R^{12}$, $NR^{5a} R^{6a}$, $OC(O)R^{7a}$ and $N(R^{10})C(O)R^{7a}$;

each $R^{8a}$ is independently $C_1$-$C_6$ alkyl or $C_1$-$C_6$ haloalkyl;

each $R^9$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11}R^{12}$, $OR^{4a}$, $C_2$-$C_6$ alkoxyalkyl, $S(O)_m R^{9a}$, $S(O)_2 NR^{11} R^{12}$, $NR^{5a} R^{6a}$, $OC(O)R^{7a}$ and $N(R^{10})C(O)R^{7a}$;

each $R^{9a}$ is independently $C_1$-$C_6$ alkyl or $C_1$-$C_6$ haloalkyl;

each $R^{10}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C(X)R^{7a}$, $C(O)OR^{8a}$, $C(O)NR^{11}R^{12}$, $S(O)_m R^{9a}$ or $S(O)_2 NR^{11} R^{12}$;

each $R^{11}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or phenyl optionally substituted with 1 to 3 substituents independently selected from the group consisting of halogen, cyano, nitro, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C(X)R^{7a}$, $C(O)OR^{8a}$, $C(O)NR^{11a}R^{12}$, $OR^{4a}$, $C_2$-$C_6$ alkoxyalkyl, $S(O)_m R^{9a}$, $S(O)_2 NR^{11a} R^{12}$, $NR^{5a} R^{6a}$, $OC(O)R^{7a}$ and $N(R^{10})C(O)R^{7a}$;

each $R^{11a}$ is independently H, $C_1$-$C_6$ alkyl, $C_2$-$C_6$ alkenyl or $C_2$-$C_6$ alkynyl;

each $R^{12}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl or $C_3$-$C_7$ cycloalkyl;

each $R^{13}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl; or $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$;

each $R^{14}$ is independently $C_3$-$C_7$ cycloalkyl, $C_4$-$C_8$ cycloalkylalkyl, $C_6$-$C_{14}$ cycloalkylcycloalkyl or $C_5$-$C_7$ cycloalkenyl, each optionally substituted with 1 to 4 substituents independently selected from the group consisting of halogen, cyano, nitro, $C_1$-$C_4$ alkyl, $C_1$-$C_4$ haloalkyl, $OR^{4a}$ and $S(O)_m R^{9a}$; or $C_1$-$C_6$ alkyl, $C_2$-$C_6$ alkenyl or $C_2$-$C_6$ alkynyl, each substituted with 1 to 4 substituents independently selected from the group consisting of cyano, nitro, $OR^4$, $NR^5 R^6$, $C(X)R^7$, $C(O)OR^8$, $C(O)NR^{11}R^{12}$, $S(O)_m R^9$ and $S(O)_2 NR^{11} R^{12}$; or phenyl, naphthalenyl or a 5- or 6-membered heteroaromatic ring, each optionally substituted with 1 to 5 substituents independently selected from the group consisting of halogen, cyano, nitro, $OR^4$, $NR^5 R^6$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_6$ alkoxyalkyl, $C(X)R^7$, $C(O)OR^8$, $C(O)NR^{11}R^{12}$, $S(O)_m R^9$, $S(O)_2 NR^{11} R^{12}$, $OC(O)R^{7a}$ and $N(R^{10})C(O)R^{7a}$; and each m is independently 0, 1 or 2.

2. A compound of claim 1 wherein:

Z is O; and

Q is phenyl or a 5- or 6-membered heteroaromatic ring, each optionally substituted with 1 to 3 substituents independently selected from the group consisting of halogen, cyano, nitro, $OR^4$, $NR^5 R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(X)NR^{11}R^{12}$, $S(O)_m R^9$, $S(O)_2 NR^{11} R^{12}$, $OC(O)R^7$ and $N(R^{10})C(O)R^7$.

3. A compound of claim 2 wherein:

Q is phenyl, pyridinyl, pyrazolyl, oxazolyl, thiazolyl, isoxazolyl, isothiazolyl, furanyl or thienyl, each optionally substituted with 1 to 3 substituents independently selected from the group consisting of halogen, cyano, nitro, $OR^4$, $NR^5 R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C(X)R^7$, $C(O)OR^8$, $C(X)NR^{11}R^{12}$, $S(O)_m R^9$, $S(O)_2 NR^{11} R^{12}$, $OC(O)R^7$ and $N(R^{10})C(O)R^7$.

4. A compound of claim 2 or 3 wherein:

each $R^1$ is independently halogen, cyano, nitro, $OR^4$, $C_1$-$C_6$ alkyl or $C_1$-$C_6$ haloalkyl;

$R^2$ is H, halogen or $C_1$-$C_6$ alkyl; and $R^3$ is H, $C(X)R^7$, $C(O)OR^8$ or $S(O)_m R^9$; or $C_1$-$C_6$ alkyl optionally substituted with 1 to 4 substituents independently selected from halogen.

5. A compound of claim 1 that is selected from the group consisting of:

N-[(2-chloro-5-methoxyphenyl)sulfonyl]-6-(trifluoromethyl)imidazo[1,2-a]pyrazine-2-carboxamide; and N-[[2-chloro-5-(trifluoromethyl)phenyl]sulfonyl]-6-(trifluoromethyl)imidazo[1,2-a]pyrimidine-2-carboxamide.

6. A composition comprising a compound of claim 1 and at least one additional component selected from the group consisting of surfactants, solid diluents and liquid diluents.

7. The composition of claim 6 wherein said composition further comprises at least one additional biologically active compound or agent.

8. The composition of claim 7 wherein the at least one additional biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluoron, borate, buprofezin, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, all strains of *Bacillus thuringiensis*, entomopathogenic bacteria, all strains of *Nucleo polyhydrosis* viruses, entomopathogenic viruses and entomopathogenic fungi.

9. The composition of claim 8 wherein the at least one additional biologically active compound or agent is selected from the group consisting of abamectin, acetamiprid, acrinathrin, amitraz, avermectin, azadirachtin, bifenthrin, buprofezin, carbaryl, cartap, chlorantraniliprole, chlorfenapyr, chlorpyrifos, clothianidin, cyantraniliprole, cyfluthrin, beta-cyfluthrin, cyhalothrin, lambda-cyhalothrin, gamma-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, all strains of *Bacillus thuringiensis* and all strains of *Nucleo polyhydrosis* viruses.

10. A method for controlling a parasitic nematode comprising contacting the parasitic nematode or its environment with a biologically effective amount of a compound of claim 1.

11. The method of claim 10 wherein the environment is a plant.

12. The method of claim 10 wherein the environment is a seed.

13. The method of claim 12 wherein the seed is coated with the compound of Formula 1, an N-oxide or salt thereof, formulated as a composition comprising a film former or adhesive agent.

14. A treated seed comprising a compound of claim 1 in an amount of from about 0.0001 to 1% by weight of the seed before treatment.

\* \* \* \* \*